(12) United States Patent
Bené et al.

(10) Patent No.: US 9,731,069 B2
(45) Date of Patent: Aug. 15, 2017

(54) PERPENDICULAR INFUSION SET AND DISPOSABLE INSERTER

(71) Applicant: Becton, Dickinson and Company, Franklin Lakes, NJ (US)

(72) Inventors: Eric Bené, Lynn, MA (US); Russell Cole, New York, NY (US); Arthur Klotz, Willow Grove, PA (US); Melissa Rosen, Lynn, MA (US); Judy Lin Walish, Brighton, MA (US); Michel Bruehwiler, Newton, MA (US); Michael Creighton, Hatboro, PA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 817 days.

(21) Appl. No.: 13/629,575

(22) Filed: Sep. 27, 2012

(65) Prior Publication Data

US 2014/0088550 A1  Mar. 27, 2014

(51) Int. Cl.
*A61M 5/158* (2006.01)
*A61M 5/162* (2006.01)
*A61M 5/142* (2006.01)

(52) U.S. Cl.
CPC ............ *A61M 5/158* (2013.01); *A61M 5/162* (2013.01); *A61M 2005/14252* (2013.01); *A61M 2005/1585* (2013.01)

(58) Field of Classification Search
CPC ................ A61M 5/162; A61M 5/2033; A61M 2005/202; A61M 2005/2026; A61M 2005/1585; A61M 2005/14252; A61M 2005/1581

See application file for complete search history.

(56) References Cited

U.S. PATENT DOCUMENTS

| | | |
|---|---|---|
| 5,522,803 A | 6/1996 | Teissen-Simony |
| 5,545,143 A | 8/1996 | Fischell |
| 5,688,254 A | 11/1997 | Lopez et al. |
| 5,776,116 A | 7/1998 | Lopez et al. |
| 5,810,792 A | 9/1998 | Fangrow et al. |
| 5,848,990 A | 12/1998 | Cirelli et al. |
| 5,851,197 A | 12/1998 | Marano et al. |
| 5,971,950 A | 10/1999 | Lopez et al. |
| 6,017,328 A | 1/2000 | Fischell et al. |
| 6,056,718 A | 5/2000 | Funderburk et al. |

(Continued)

FOREIGN PATENT DOCUMENTS

| | | |
|---|---|---|
| EP | 1743667 A2 | 1/2007 |
| EP | 2457603 A1 | 5/2012 |
| WO | 2008051920 A2 | 5/2008 |

*Primary Examiner* — Laura Bouchelle
*Assistant Examiner* — Justin L Zamory
(74) *Attorney, Agent, or Firm* — Dickinson Wright PLLC

(57) ABSTRACT

An infusion set is disclosed that includes an inserter including an inserter housing having at least one flexible arm for holding an infusion set in a single axial position prior to insertion of at least a portion of a cannula of the infusion set, the inserter housing having a surface for contacting the patient's skin. The inserter also includes a movable plunger disposed within the inserter housing for releasing the infusion set from the inserter housing, impacting the infusion set, and imparting momentum to the infusion set to insert the cannula into the patient's skin. The inserter additionally includes a biasing element biasing the plunger toward the activated position.

24 Claims, 27 Drawing Sheets

(56) References Cited

U.S. PATENT DOCUMENTS

| | | | |
|---|---|---|---|
| 6,093,172 A | 7/2000 | Funderburk et al. | |
| 6,293,925 B1 * | 9/2001 | Safabash | A61M 5/158 604/136 |
| 6,302,866 B1 | 10/2001 | Marggi | |
| 6,355,021 B1 | 3/2002 | Nielsen et al. | |
| 6,607,509 B2 | 8/2003 | Bobroff et al. | |
| 6,685,674 B2 | 2/2004 | Douglas et al. | |
| 6,736,797 B1 | 5/2004 | Larsen et al. | |
| 6,830,562 B2 | 12/2004 | Mogensen et al. | |
| 6,840,922 B2 | 1/2005 | Nielsen et al. | |
| 6,890,319 B1 | 5/2005 | Crocker | |
| 6,926,694 B2 | 8/2005 | Marano-Ford et al. | |
| 6,949,084 B2 | 9/2005 | Marggi et al. | |
| 6,997,907 B2 | 2/2006 | Safabash et al. | |
| 7,056,302 B2 | 6/2006 | Douglas et al. | |
| 7,070,580 B2 | 7/2006 | Nielsen | |
| 7,128,727 B2 | 10/2006 | Flaherty et al. | |
| 7,207,974 B2 | 4/2007 | Safabash et al. | |
| 7,211,068 B2 | 5/2007 | Douglas | |
| 7,297,138 B2 | 11/2007 | Fangrow et al. | |
| 7,300,419 B2 | 11/2007 | Fangrow et al. | |
| 7,318,816 B2 | 1/2008 | Bobroff et al. | |
| 7,329,239 B2 | 2/2008 | Safabash et al. | |
| 7,331,939 B2 | 2/2008 | Fangrow et al. | |
| 7,407,491 B2 | 8/2008 | Fangrow et al. | |
| 7,407,493 B2 | 8/2008 | Cane | |
| 7,494,481 B2 | 2/2009 | Moberg et al. | |
| 7,520,867 B2 | 4/2009 | Bowman et al. | |
| 7,585,287 B2 | 9/2009 | Bresina et al. | |
| 7,699,807 B2 | 4/2010 | Faust et al. | |
| 7,699,808 B2 | 4/2010 | Marrs et al. | |
| 7,731,691 B2 | 6/2010 | Cote et al. | |
| 7,736,338 B2 | 6/2010 | Kavazov et al. | |
| 7,744,568 B2 | 6/2010 | Douglas et al. | |
| 7,744,570 B2 | 6/2010 | Fangrow | |
| 7,771,393 B2 | 8/2010 | Liniger et al. | |
| 7,815,607 B2 | 10/2010 | Rutti et al. | |
| 7,879,010 B2 | 2/2011 | Hunn et al. | |
| 7,892,216 B2 | 2/2011 | Fangrow | |
| 7,896,844 B2 | 3/2011 | Thalmann et al. | |
| 7,931,615 B2 | 4/2011 | Fangrow | |
| 8,152,769 B2 | 4/2012 | Douglas et al. | |
| 8,152,771 B2 | 4/2012 | Mogensen et al. | |
| 8,162,892 B2 | 4/2012 | Mogensen et al. | |
| 8,172,805 B2 | 5/2012 | Mogensen et al. | |
| 2003/0109829 A1 * | 6/2003 | Mogensen | A61M 5/158 604/164.01 |
| 2003/0199823 A1 | 10/2003 | Bobroff et al. | |
| 2005/0090784 A1 | 4/2005 | Nielsen et al. | |
| 2006/0135908 A1 * | 6/2006 | Liniger | A61M 5/158 604/93.01 |
| 2006/0217663 A1 | 9/2006 | Douglas | |
| 2007/0093754 A1 | 4/2007 | Mogensen et al. | |
| 2007/0185454 A1 | 8/2007 | Fangrow | |
| 2007/0276355 A1 | 11/2007 | Nielsen et al. | |
| 2008/0114280 A1 | 5/2008 | Stafford | |
| 2008/0215035 A1 | 9/2008 | Yodfat et al. | |
| 2009/0076453 A1 | 3/2009 | Mejlhede et al. | |
| 2009/0124979 A1 | 5/2009 | Raymond et al. | |
| 2009/0143763 A1 | 6/2009 | Wyss et al. | |
| 2009/0264825 A1 | 10/2009 | Cote et al. | |
| 2010/0030148 A1 | 2/2010 | Alchas et al. | |
| 2010/0100050 A1 | 4/2010 | Cane | |
| 2010/0217105 A1 | 8/2010 | Yodfat et al. | |
| 2011/0028982 A1 * | 2/2011 | Lacy | A61M 5/158 606/108 |
| 2011/0040256 A1 | 2/2011 | Bobroff et al. | |
| 2011/0060287 A1 * | 3/2011 | Ambruzs | A61M 5/158 604/164.12 |
| 2011/0087196 A1 | 4/2011 | Hunn et al. | |
| 2011/0257597 A1 | 10/2011 | Safabash et al. | |
| 2012/0143135 A1 * | 6/2012 | Cole | A61M 5/158 604/164.04 |
| 2012/0143136 A1 * | 6/2012 | Constantineau | A61M 5/158 604/164.04 |

* cited by examiner

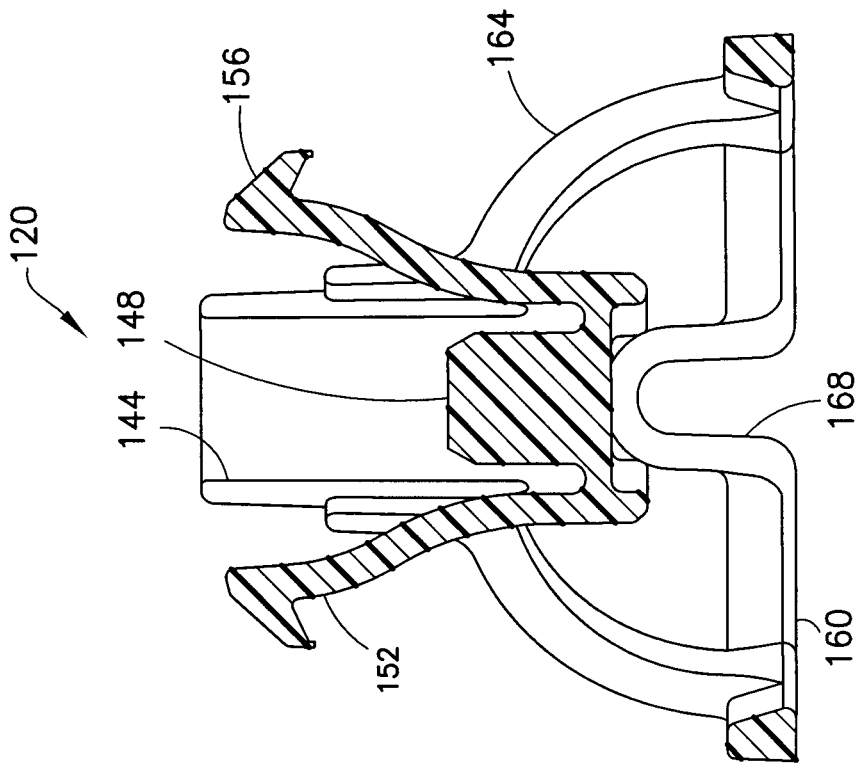
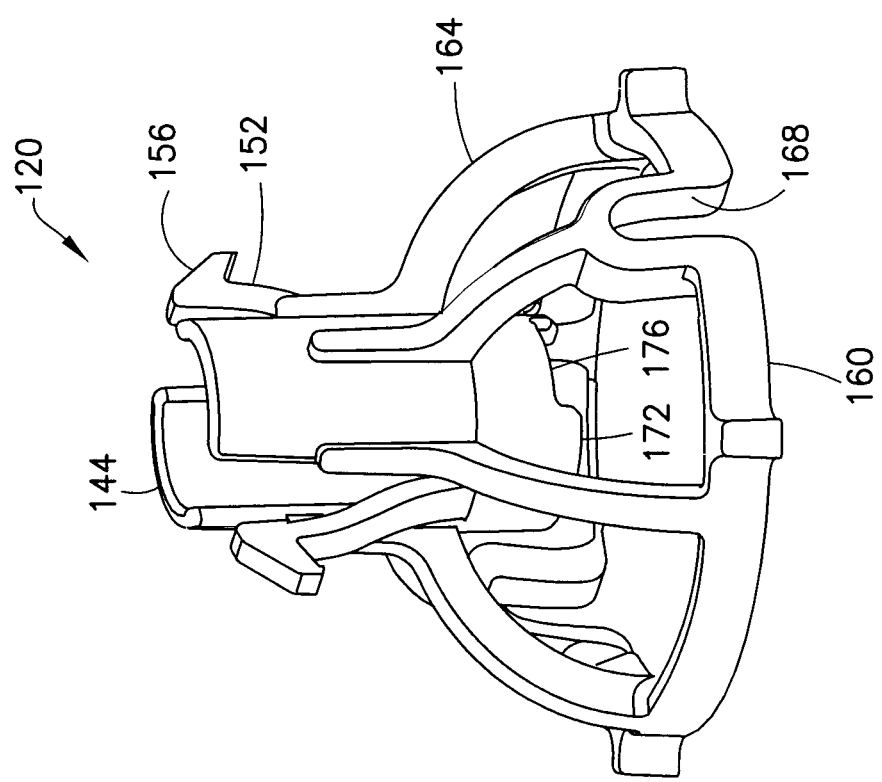

PERPENDICULAR INFUSION SET AND DISPOSABLE INSERTER

BACKGROUND OF THE INVENTION

1. Field of the Invention

The present invention relates to a medical insertion device assembly, and more particularly, to an intradermal infusion set and an inserter therefor.

2. Description of the Related Art

A large number of people, including those suffering from conditions such as diabetes use some form of infusion therapy, such as daily insulin infusions to maintain close control of their glucose levels. There are two principal modes of daily insulin therapy. The first mode includes syringes and insulin pens. These devices are simple to use and are relatively low in cost, but they require a needle stick at each injection, typically three to four times per day. The second mode includes infusion pump therapy, which entails the purchase of an insulin pump that lasts for about three years. The initial cost of the pump can be significant, but from a user perspective, the overwhelming majority of patients who have used pumps prefer to remain with pumps for the rest of their lives. This is because infusion pumps, although more complex than syringes and pens, offer the advantages of continuous infusion of insulin, precision dosing and programmable delivery schedules. This results in closer blood glucose control and an improved feeling of wellness.

The use of an infusion pump requires the use of a disposable component, typically referred to as an infusion set or pump set, which conveys the insulin from a reservoir within the pump into the skin of the patient. An infusion set typically consists of a pump connector, a length of tubing, and a hub or base from which an infusion needle or cannula extends. The hub or base has an adhesive which retains the base on the skin surface during use, which may be applied to the skin manually or with the aid of a manual or automatic insertion device.

Currently, most insulin infusion sets deliver insulin to the subcutaneous layers of skin using either fixed metal needles or flexible plastic cannulas. Such infusion sets typically deliver insulin 4-10 mm below the skin surface. However, the upper 3 mm of skin surface, the intradermal space, facilitates better drug absorption. Unfortunately, due to the relative thinness of the intradermal layer, inserting a needle at such depth and maintaining an infusion site over an extended period of time within this narrow band is difficult.

Further, most insulin infusion sets typically do not provide any features to isolate the inserted needle or cannula from shock or other external forces. Since these infusion sets typically deliver insulin 4-10 mm below the skin surface, shock or other external forces to the set have less effect on the deeper inserted needle or cannula. But where an attempt is made to target the upper 3 mm of skin surface, any shock or movement of the set can adversely affect needle insertion and infusion performance.

Still further, most insulin infusion sets use inserters that can result in skin surface "tenting" during needle insertion, where the skin surface is deflected somewhat prior to or during needle insertion which makes precisely targeting the upper 3 mm of skin surface difficult. Moreover, with many inserters, after insertion of the infusion set, the user must take the additional step of removing or separating the inserter from the infusion device. This action can displace the inserted infusion set even if there is an adhesive on the bottom of the infusion set.

Accordingly, a need exists for an infusion set that can deliver content to the upper 3 mm of skin surface, the intradermal space, to facilitate better drug absorption, while maintaining a degree of comfort to the user. Further, it is desirable to avoid infusion set displacement after insertion, particularly for intradermal infusion sets having short infusion needles.

SUMMARY OF EMBODIMENTS OF THE INVENTION

Accordingly, it is an aspect of the present invention to provide an infusion set and an inserter that can insert the infusion set to deliver content to the intradermal space, to facilitate better drug absorption, while maintaining a degree of comfort to the user. It is another aspect of the invention to provide an inserter that avoids infusion set displacement after insertion.

The foregoing and/or other aspects of the present invention are achieved by providing an infusion set inserter including an inserter housing having at least one flexible arm for holding an infusion set in a single axial position prior to insertion of at least a portion of a cannula of the infusion set, the inserter housing having a surface for contacting the patient's skin. The inserter also includes a movable plunger disposed within the inserter housing for releasing the infusion set from the inserter housing, impacting the infusion set, and imparting momentum to the infusion set to insert the cannula into the patient's skin. The inserter additionally includes a biasing element biasing the plunger toward the activated position.

The foregoing and/or other aspects of the present invention are also achieved by providing an infusion set inserter including an inserter housing for holding an infusion set in a single axial position prior to insertion of at least a portion of a cannula of the infusion set, the inserter housing having a surface for contacting the patient's skin. The inserter also includes a movable plunger disposed within the inserter housing for releasing the infusion set from the inserter housing, impacting the infusion set, and imparting momentum to the infusion set to insert the cannula into the patient's skin. The plunger includes a cantilevered arm with a hook disposed at a free end thereof for contacting the inserter housing to selectively retain the plunger in a pre-activated position prior to activation. The inserter additionally includes a biasing element biasing the plunger toward the activated position.

The foregoing and/or other aspects of the present invention are also achieved by providing a method of inserting at least a portion of a cannula of an infusion set into a patient's skin. The method includes maintaining the infusion set in a single axial position in an inserter housing a at least one flexible arm of the inserter housing, and placing the inserter housing on the patient's skin over an intended infusion site. The method also includes releasing a biased plunger to move within the inserter. Movement of the plunger releases the infusion set from the inserter housing, impacts the infusion set, and imparts momentum to the infusion set to insert the cannula into the patient's skin.

The foregoing and/or other aspects of the present invention are also achieved by providing an insertion device assembly including an infusion set and an infusion set inserter. The infusion set includes a base with a port disposed on a first side thereof and a cannula disposed on an opposing, second side thereof, the second side having at least one detent recessed from the surface thereof. The inserter includes an inserter housing for holding the infusion set, the inserter housing including a surface for contacting the patient's skin and at least one arm for selectively engaging the detent in the infusion set base to maintain the infusion set within the inserter housing, a movable plunger disposed within the inserter housing, and a biasing element biasing the plunger toward a patient end of the inserter housing.

The foregoing and/or other aspects of the present invention are also achieved by providing an infusion set that includes a base, a self-sealing septum, and a fluid connector for connection with an external pump, the fluid connector being lockable to the base. The base includes a first side, an opposing, second side for contacting a patient's skin, a base cannula extending from the second side in a second direction for insertion into the patient's skin, an engaging protrusion extending in the first direction from the first side of the base, and a locking structure that one of extends in the first direction from the top side of the base or is recessed from the first side of the base. The self-sealing septum is disposed within a fluid path between the port and the cannula.

The fluid connector includes a connector cannula for insertion through the port and the septum when the fluid connector is connected with the base, and a first connector for rotatably engaging the engaging protrusion to prevent displacement of the fluid connector in the first direction relative to the base and prevent rotation of the fluid connector in a single, first rotational direction relative to the base. The fluid connector also includes a second connector for engaging the locking structure to prevent rotation of the fluid connector in a second rotational direction opposite to the first rotational direction but permit displacement of the fluid connector in the first direction relative to the base.

Additional and/or other aspects and advantages of the present invention will be set forth in the description that follows, or will be apparent from the description, or may be learned by practice of the invention.

BRIEF DESCRIPTION OF THE DRAWINGS

The above and/or other aspects and advantages of embodiments of the invention will become apparent and more readily appreciated from the following detailed description, taken in conjunction with the accompanying drawings, in which:

FIG. 3 is a perspective view of a plunger of the assembly of FIG. 1;

FIG. 4 is a cross-sectional view of the plunger of FIG. 3;

DETAILED DESCRIPTION OF EMBODIMENTS OF THE PRESENT INVENTION

Figure 1:
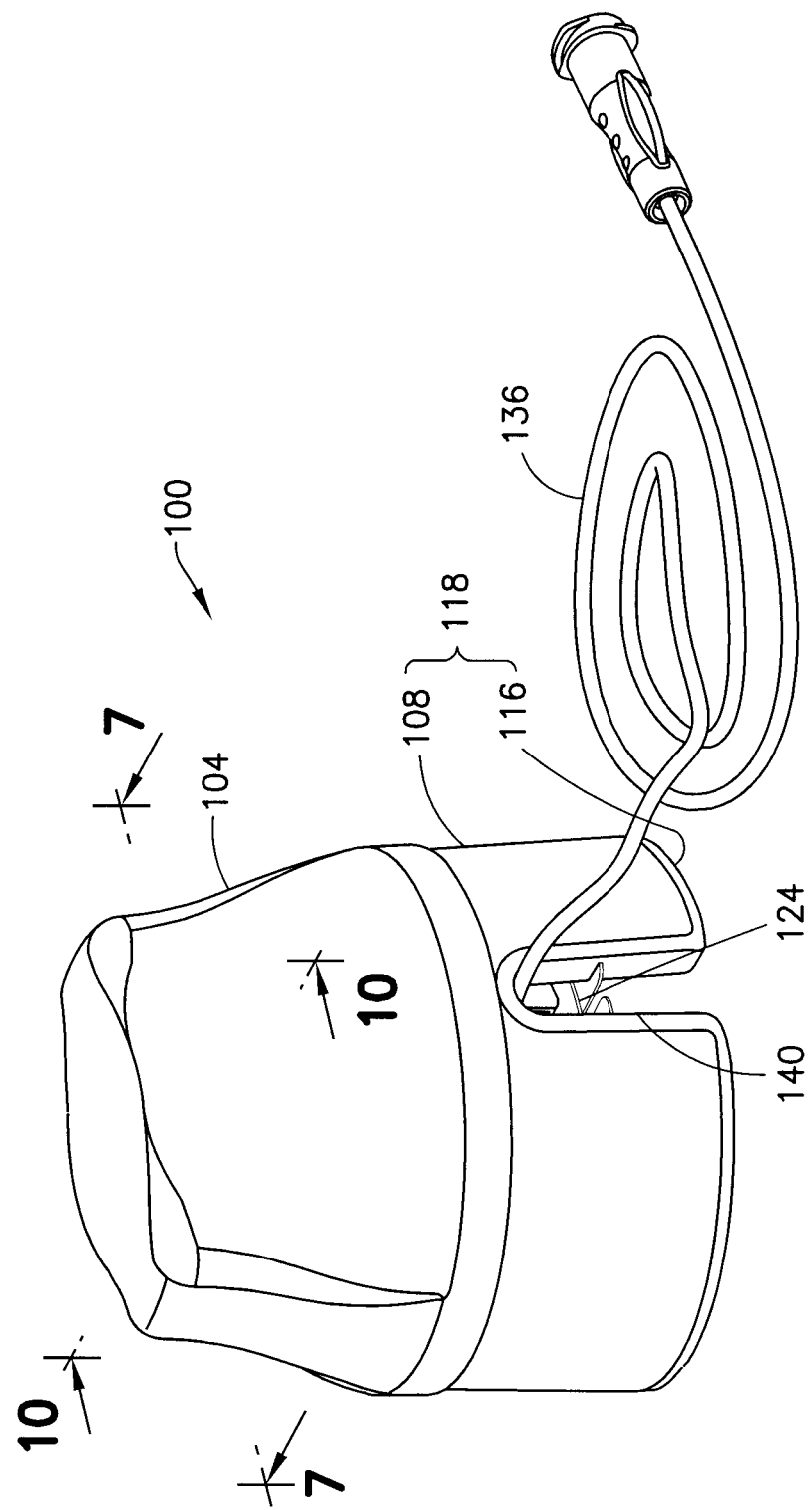
FIG. 1 is a perspective view of an insertion device assembly in accordance with an embodiment of the present invention.

Reference will now be made in detail to embodiments of the present invention, which are illustrated in the accompanying drawings, wherein like reference numerals refer to like elements throughout. The embodiments described herein exemplify, but do not limit, the present invention by referring to the drawings. As will be understood by one skilled in the art, terms such as up, down, bottom, and top are relative, and are employed to aid illustration, but are not limiting.

Figure 2:
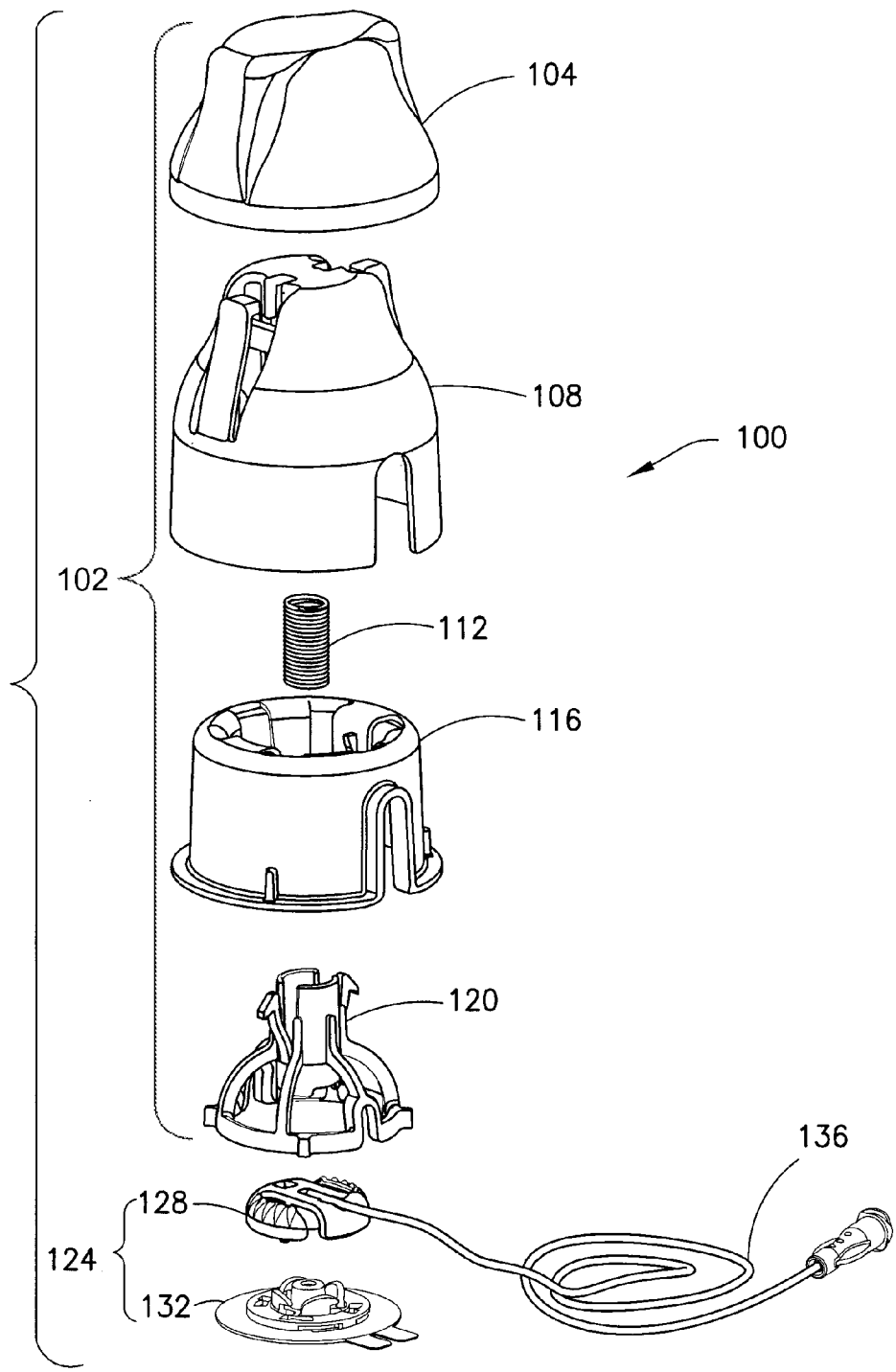
FIG. 2 is an exploded view of the assembly of FIG. 1.

FIGS. 1 and 2 illustrate an insertion device assembly 100 in accordance with an embodiment of the present invention. As shown in FIGS. 1 and 2, the insertion device assembly includes an infusion set inserter 102 and an infusion set 124, which, according to one embodiment, are advantageously sold as a unit (i.e., with the infusion set 124 pre-installed in the inserter 102). The infusion set inserter 102 or inserter 102 includes an inserter cover 104, an inserter cap 108, a biasing member 112, such as a spring 112, an inserter base 116, and a plunger 120. As will be described in greater detail below, the infusion set 124 includes a fluid connector 128 and an infusion set base 132 or base 132. According to one embodiment, the infusion set 124 also includes tubing 136 for connecting the infusion set 124 with a pump.

Preferably, the inserter cover 104, the inserter cap 108, the inserter base 116, the plunger 132, the fluid connector 128, and the base 132 are made of injection-molded plastic. For example, the inserter cover 104, the fluid connector 128, and the base 132 are preferably made of polyethylene terephtalate glycol-modified (PETG), and the inserter cap 108 and the inserter base 116 are made of acrylonitrile butadiene styrene (ABS). Additionally, the plunger is preferably made of acetal. Further, the biasing member 112 is preferably a metal coil spring. In addition, an intradermal cannula or patient needle 292 (see, for example, FIGS. 7 and 17) that extends approximately 1.5 mm from the lowest surface of the base 132 is preferably a 34 gauge needle 292 made of stainless steel. The patient needle 292 is hollow and communicates with the tubing 136 (shown, for example, in FIG. 1).

The inserter cap 108 is secured to the inserter base 116, and together, they form an inserter housing 118. As shown in FIG. 1, the inserter housing 118 includes a case tube opening 140 to accommodate the tubing 136 both prior to and subsequent to activation of the inserter 102.

Figure 5:
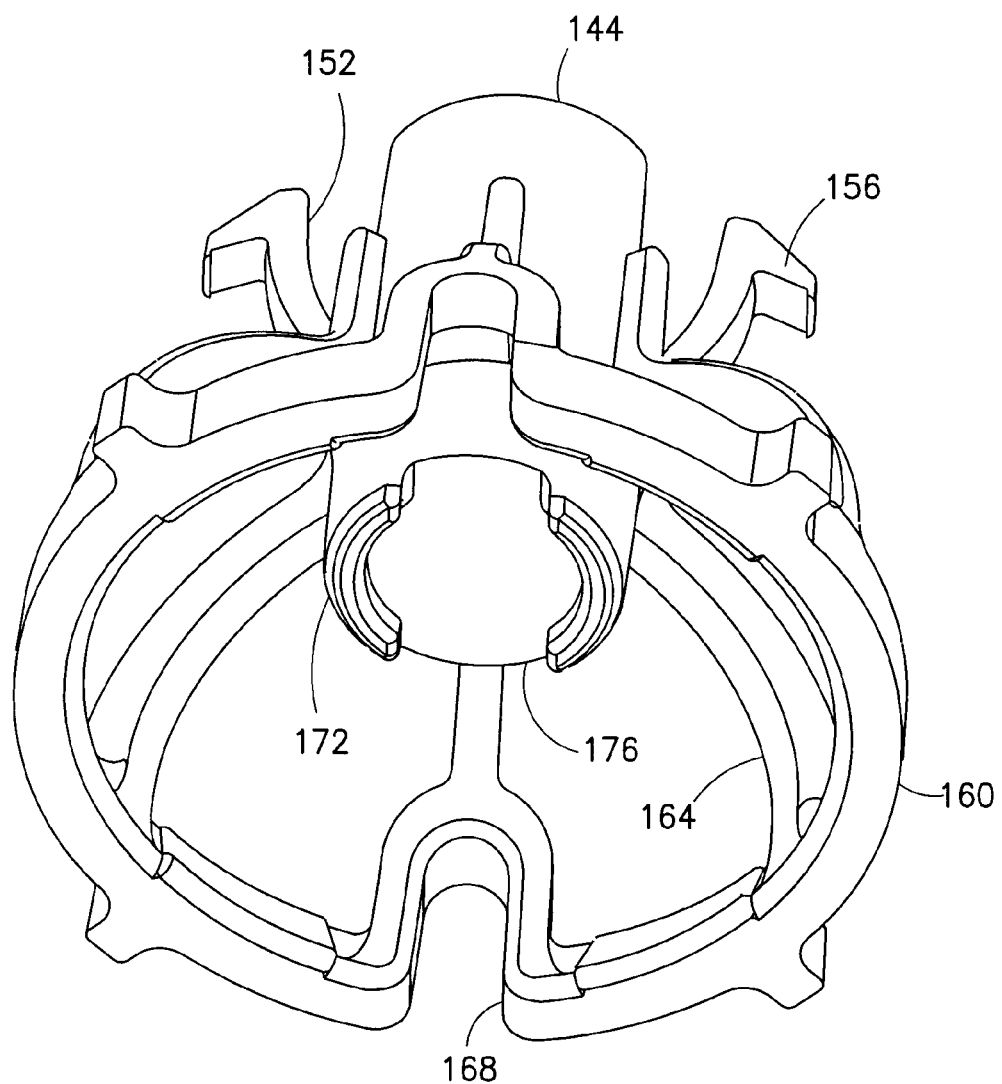
FIG. 5 is a perspective view of a bottom of the plunger of FIG. 3.

FIGS. 3-5 illustrate the plunger 120 in greater detail. The plunger 120 includes a spring receiving portion 144 for accommodating one end of the spring 112. The spring receiving portion 144 has a central protrusion 148 for securing the end of the spring 112. The plunger 120 also includes a pair of cantilevered plunger arms 152 that respectively have plunger hooks 156 on the unsupported ends thereof. Additionally, the plunger 120 includes a collar or ring structure 160 connected to the spring receiving portion 144 by a plurality of legs 164. The ring structure 160 and the legs 164 include a tubing opening 168 to accommodate the tubing 136. A hammer portion 172 for impacting or striking the infusion set 124 is disposed on the bottom of the spring receiving portion 144. The hammer portion 172 also has a tubing opening 176 to accommodate the tubing 136.

Figure 6:
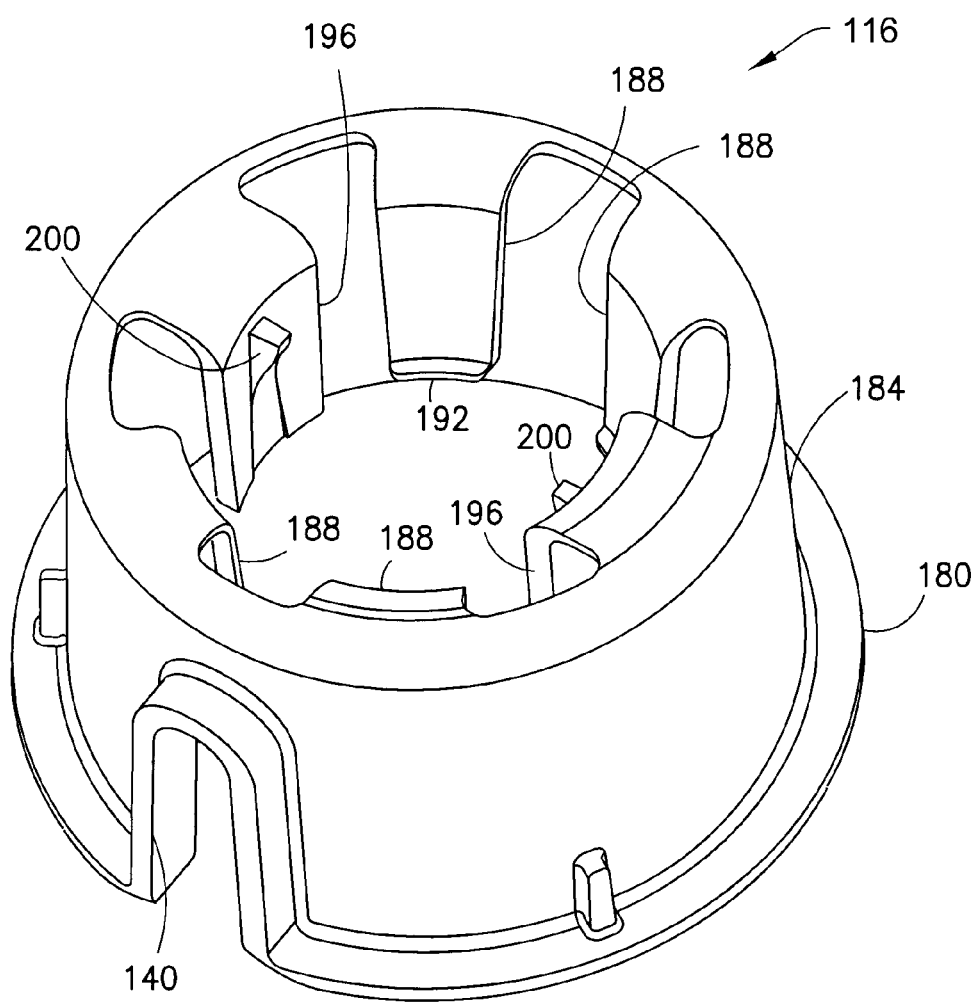
FIG. 6 is a perspective view of an inserter base of the assembly of FIG. 1.

As shown in FIG. 6, the inserter base 116 includes a flange 180 and an outer wall 184. The bottom or distal side of the flange 180 has a surface for contacting the skin of the patient. The inserter base 116 also includes a plurality of flexible cantilevered arms on the interior thereof. According to one embodiment, there are two varieties of these cantilevered arms: those having feet and those without. As will be discussed in greater detail below, the arms 188 with feet 192 can be characterized as active arms 188, and the arms 196 without feet can be characterized as passive arms 196. Also discussed in greater detail below, the passive arms 196 include plunger stops 200.

Figure 7:
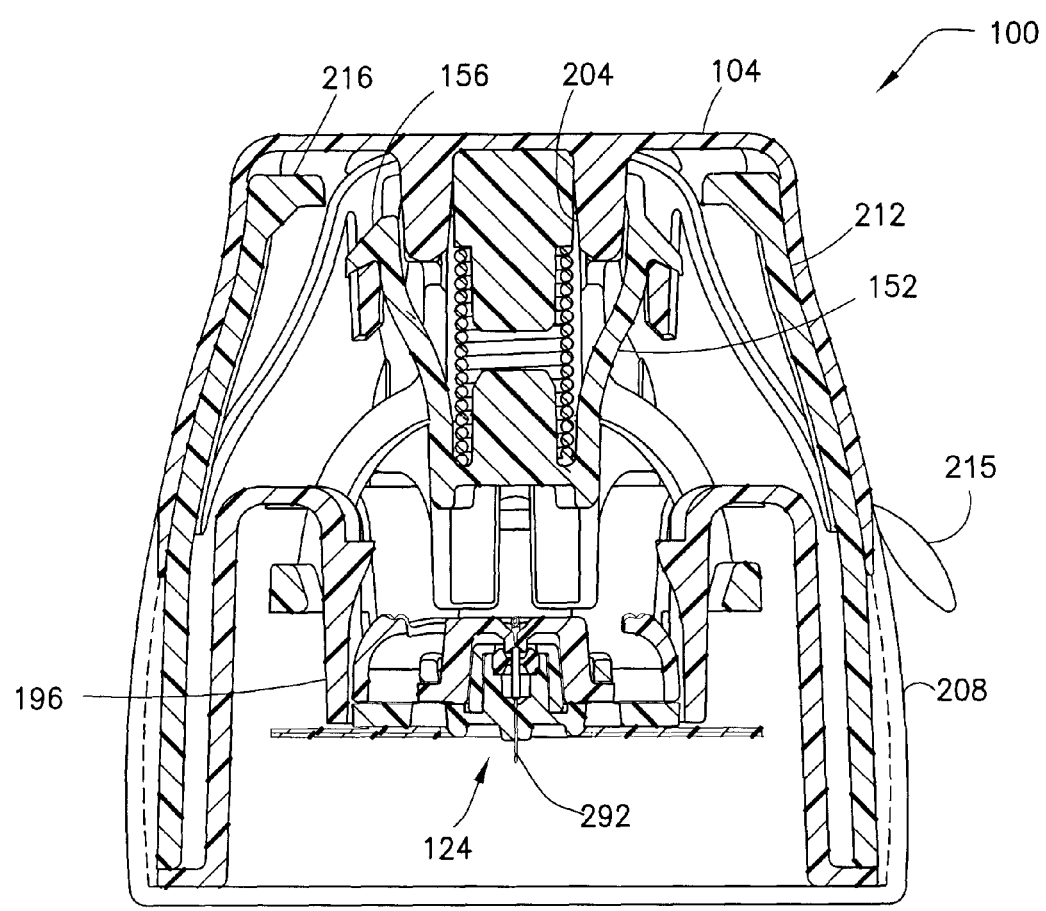
FIG. 7 is a cross-sectional view of the assembly of FIG. 1 taken along line 7-7 of FIG. 1.

As shown in FIG. 7, the inserter cover 104 includes a pair of safety structures 204 that prevent inward radial displacement of the plunger arms 152, and therefore prevent accidental activation of the inserter 102. According to one embodiment, shown in dotted line in FIG. 7, the inserter cover 104 extends all the way to the bottom more distal end of the inserter 102. Additionally, according to one embodiment, the assembly 100 includes a user-removable membrane 208 to maintain the sterility of the interior the assembly 100. The membrane 208 can have a tab 215 to aid user removal of the membrane 208, and, according to one embodiment, can cover the case tubing opening 140. According to one embodiment, removal of the membrane 208 also removes a backing to an adhesive pad on the bottom of the infusion set 124.

Figure 8:
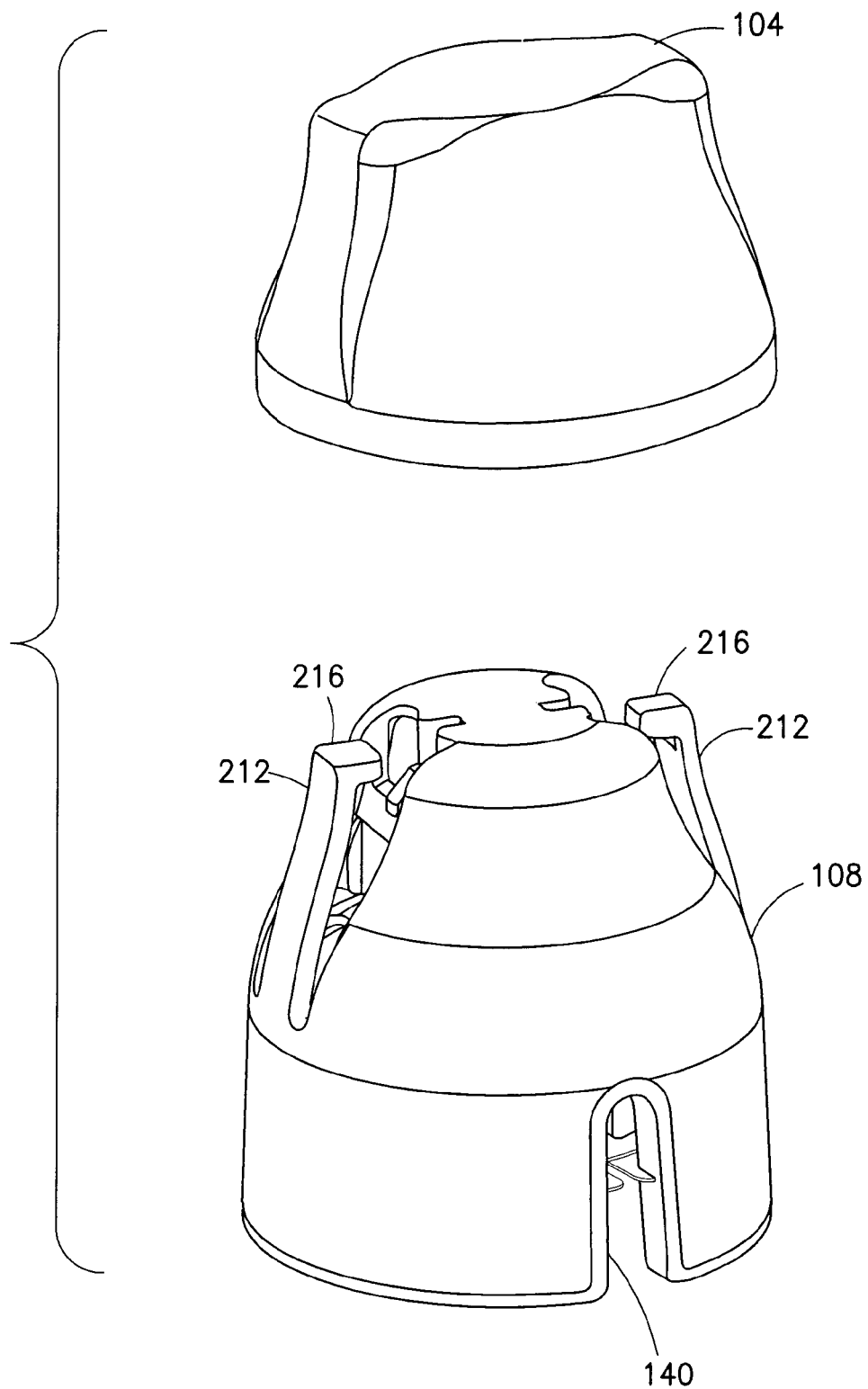
FIG. 8 is a perspective view of a cap being removed from the assembly of FIG. 1.

Subsequent to removal of the membrane 208, as shown in FIG. 8, removal of the inserter cover 104 exposes cantilevered activation arms 212 of the inserter cap 108. The activation arms 212 include activation protrusions 216 at the unsupported ends thereof. Additionally, like the plunger 120, the inserter cover 104 includes a central protrusion 220 to accommodate the spring 112, which is shown more clearly in FIGS. 9 and 10.

Figure 9:
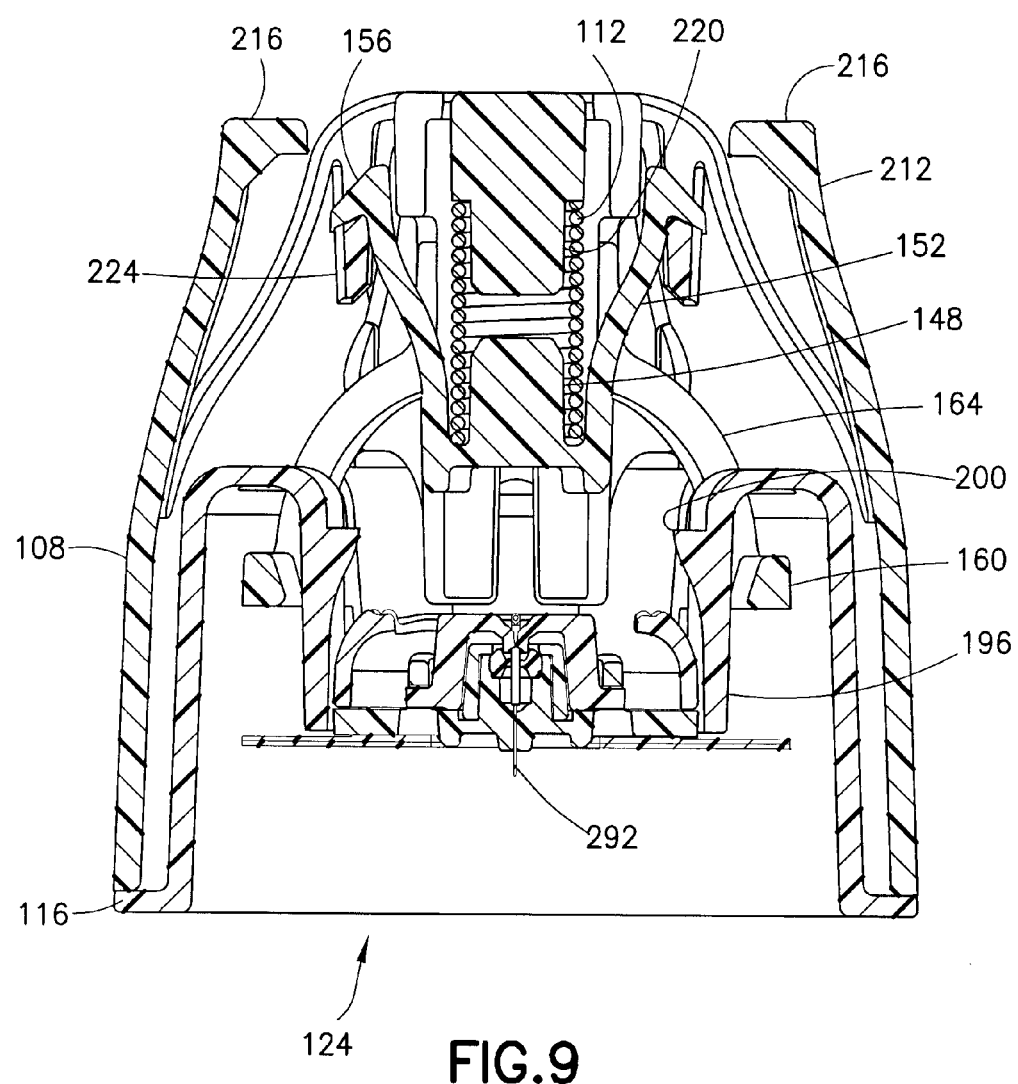
FIGS. 9 and 10 are cross-sectional views of the assembly of FIG. 1 respectively taken along lines 7-7 and 10-10 of FIG. 1, and illustrate the plunger of FIG. 3 in a pre-activated position.
Figure 10:
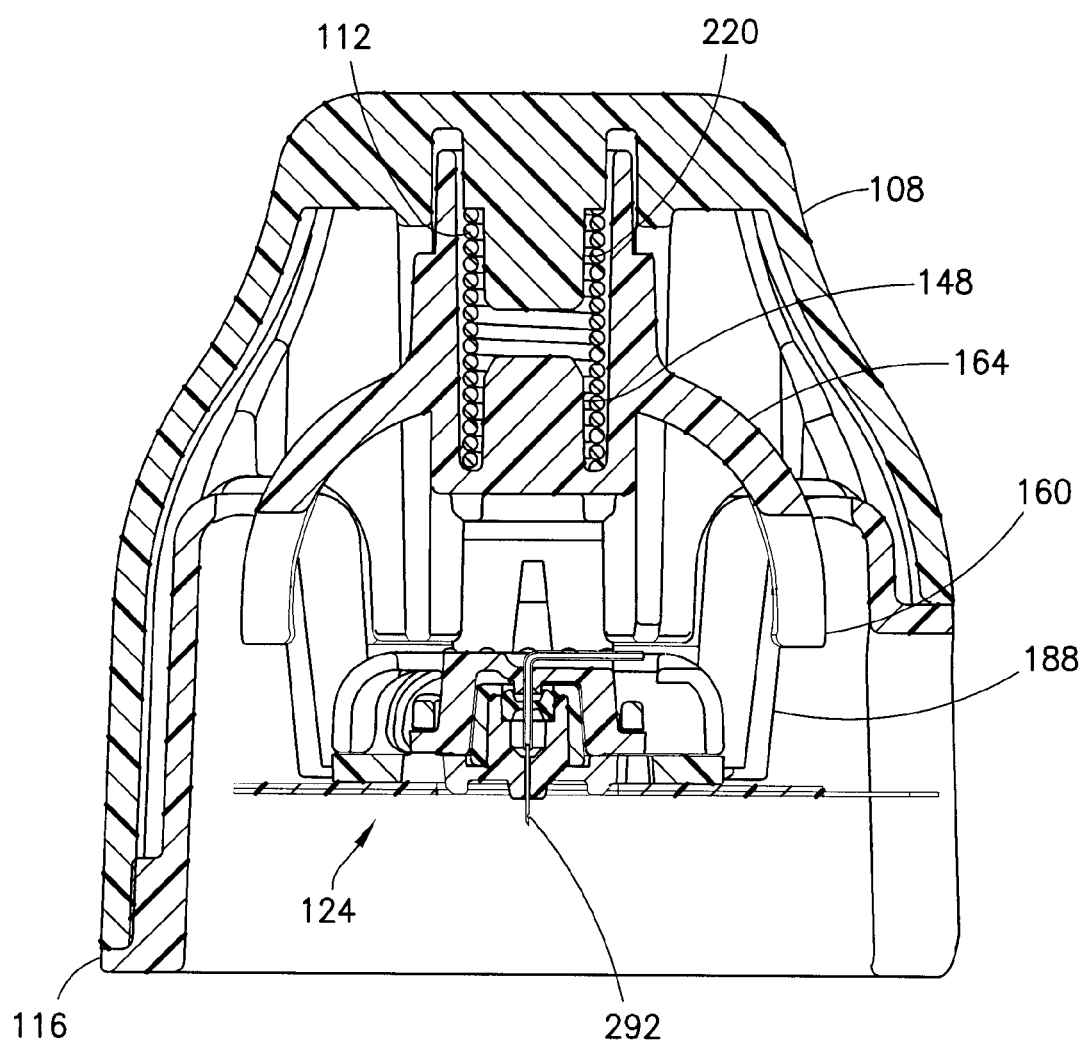

FIGS. 9 and 10 are cross-sectional views respectively taken along lines 7-7 and 10-10 of FIG. 1, and illustrate the inserter 102 in a pre-activated state, in which the plunger 120 is in a pre-activated position. In the pre-activated position, the ring structure 160 contacts the cantilevered arms 188 and pulls them radially inward, thereby biasing the arms 188 toward the infusion set 124. As described in greater detail below, with the plunger 120 in the pre-activated position, the feet 192 of the arms 188 engage detents in the bottom or distal surface of the infusion set 124. In combination with the contact between the arms 196 and the infusion set 124, this contact prevents movement the infusion set 124 within the inserter 102 prior to activation. In other words, the arms 188 and 196 hold the infusion set 124 in a single axial position relative to the inserter housing 118. According to one embodiment, in this position, the infusion set 124 is spaced apart from the patient's skin. According to another embodiment, the distal end of the cannula can be in contact with the patient's skin.

According to one embodiment, in the pre-activated position, the ring structure 160 also pulls the arms 196 radially inward, but to a lesser degree than the arms 188. Further, as shown in FIG. 9, in the pre-activated position, the hooks 156 of the plunger arms 152 engage plunger-retaining structures 224 of the inserter cap 108.

Although it is not necessary for the patient to be the one who activates the inserter 102, for brevity and clarity, it will be assumed hereinafter that the patient is acting alone. To activate the device, the patient squeezes the activation arms 212 so that the activation protrusions 216 disengage the plunger hooks 156 from the plunger-retaining structures 224. Then, under the force of the spring 112, the plunger 120 travels from the pre-activated position to an activated position, which is illustrated in FIG. 11.

As the plunger 120 travels from the pre-activated position to the activated position, the ring structure 160 disengages from the cantilevered arms 188 and 196, thereby permitting the arms 188 to return to their unbiased position in which the feet 192 no longer engage the detents in the bottom of the infusion set 124. Once the ring structure 160 disengages from the cantilevered arms 188 and 196, the arms 196 still compressively engage the sides of the infusion set 124. Subsequently, the hammer portion 172 impacts or strikes the infusion set 124, driving the infusion set out of contact with the arms 196 and into the patient's skin. In other words, this collision between the plunger 120 and the infusion set 124 releases the infusion set 124 from the inserter 102 and imparts momentum to the infusion set 124 to insert the cannula or patient needle 292 of the infusion set 124 into the patient's skin.

According to one embodiment, after the impact, the infusion set 124 moves free of the inserter 102 and the plunger 120 under the momentum imparted by the plunger 120. Put another way, the plunger 120 does not contact the infusion set 124 during insertion of the patient needle 292. According to one embodiment, however, the hammer portion 172 can contact the infusion set 124 again after insertion. According to yet another embodiment, the plunger 120 strikes the infusion set 124, remains in contact with the infusion set 124, and drives the infusion set 124 to insert the patient needle 292.

Figure 11:
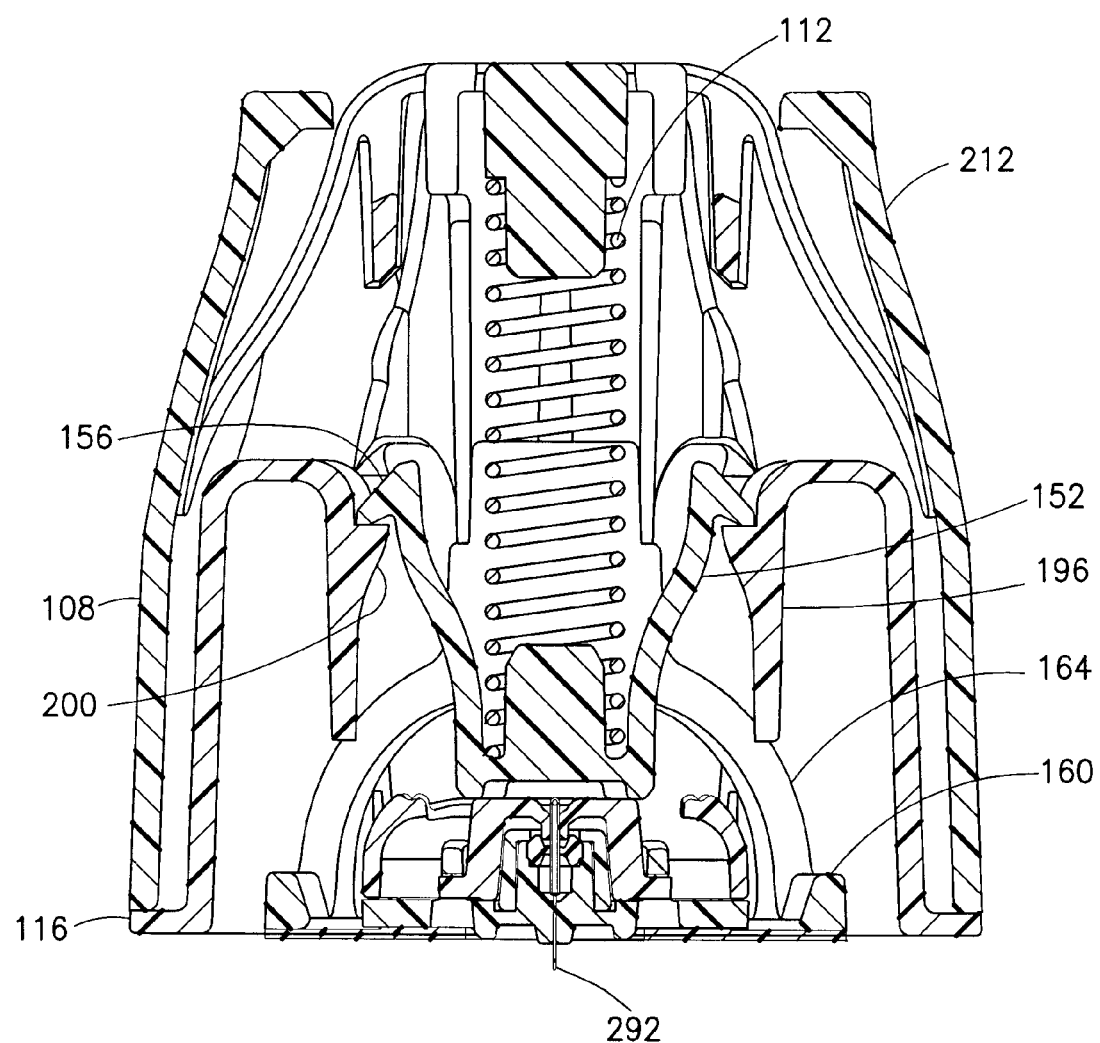
FIG. 11 is a cross-sectional view illustrating the plunger of FIG. 3 in an activated position.
Figure 12:
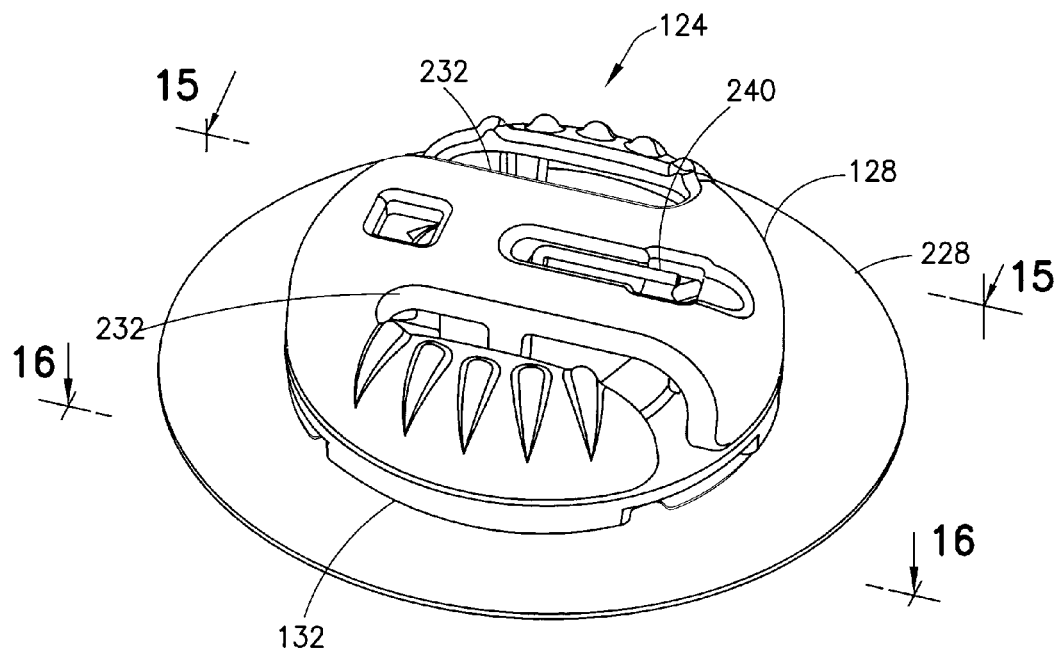
FIG. 12 is a perspective view of an infusion set of the assembly of FIG. 1.
Figure 13:
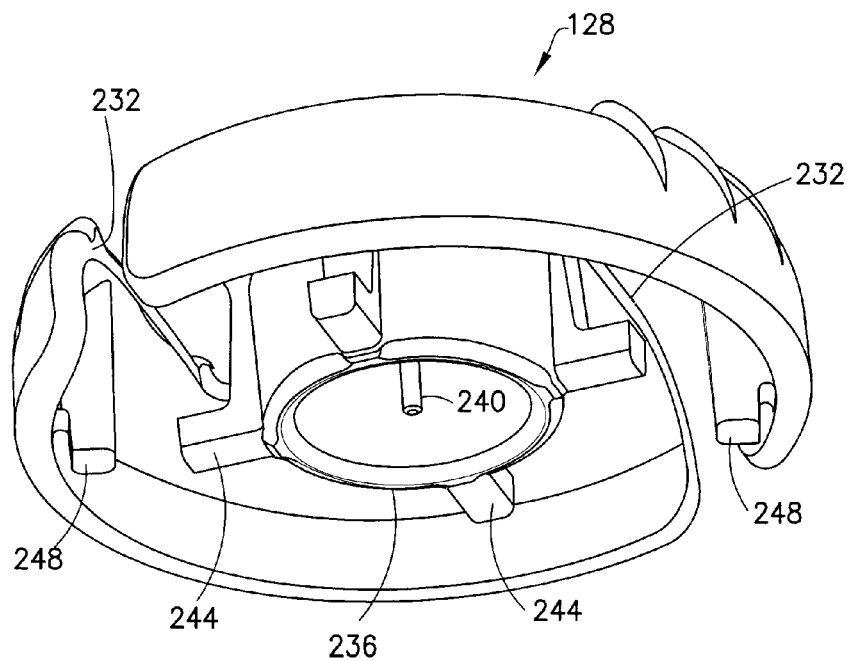
FIG. 13 is a perspective view of the bottom of a fluid connector of the infusion set of FIG. 12.

As shown in FIG. 11, in the activated position, the plunger stops 200 engage the plunger hooks 156 to retain the plunger 120 within the inserter housing 118.

According to one embodiment, disengagement of the ring structure from the arms 188 does not disengage the feet 192 from the detents in the bottom of the infusion set 124. In other words, in the unbiased positions of the arms 188, the feet 192 remain engaged with the detents. In this embodiment, the impact of the hammer portion 172 disengages the infusion set from the feet 192 and arms 188. Additionally, according to one embodiment, all of the cantilevered arms 188 and 196 have feet 192.

According to another embodiment, referring to FIGS. 9-11, rather than pulling the arms 188 or 196 radially inward, in the pre-activated position, the ring structure 160 prevents the arms 188 and 196 from displacing radially outward. Then, after moving from the pre-activated position to the activated position, the ring structure 160 no longer prevents the arms 188 and 196 from displacing radially outward. The impact of the plunger 120 releases the infusion set 124 from the arms 188 and 192 and imparts momentum to insert the cannula 292 into the patient's skin.

According to one embodiment, the inserter 102 is a single-use device, with the infusion set 124 being prepackaged within the inserter 102. According to another embodiment, although the infusion set 124 can be prepackaged within the inserter 102, the inserter 102 can be reused. Alternatively, the reusable inserter 102 can be separate from the infusion set 124. In this reusable embodiment, to move the plunger 120 to the pre-activated position, the inserter cover 104 is removed, thus enabling the plunger arms 152 to move radially to engage the plunger hooks 156 with the plunger retaining structures 224. According to one embodiment (not shown), the plunger 120 includes a handle protruding through the inserter cap 108 to aid the patient in moving the plunger 120 to the pre-activated position. According to another embodiment, the patient presses the plunger 120 upward to move it to the pre-activated position. In one embodiment, the patient loads the infusion set 124 into the inserter 102 prior to moving the plunger 120 to the pre-activated position. According to an alternative embodiment, the patient loads the infusion set 124 into the inserter 102 subsequent to moving the plunger 120 to the pre-activated position.

Although the illustrated embodiments depict the infusion set 124, it will be understood by one skilled in the art that other infusion sets can be used with the inserter 102 without departing from the scope of the present invention.

As shown in FIGS. 12-18, the infusion set 124 includes a fluid connector 128, a base 132, and an adhesive pad 228. As will be discussed in greater detail below, to remove the fluid connector 128 from the base 132, the fluid connector 128 includes a pair of opposingly oriented cutouts 232 to facilitate compression of the sides. Looking at the underside of the fluid connector 128 in FIG. 13, a substantially cylindrical guide 236 is disposed in the middle of the fluid connector 128. According to another embodiment, the guide 236 is frustoconical. Centrally located within the guide 236, a fluid connector cannula 240 depends from the fluid connector 128. According to one embodiment, the cannula 240 is bent at approximately 90° and extends out of the top of the fluid connector to connect with the tubing 136, which is omitted from FIG. 12 for clarity. According to one embodiment, the cannula 240 is made of metal. According to another embodiment, the cannula is plastic and is integrally formed with the fluid connector 128.

Additionally, the fluid connector 128 has a two-part connector for connecting with the base 132, including first connectors 244 (or L-shaped legs 244) and second connectors 248 (or cantilevered connector tabs 248). As described in greater detail below, once connected to the base 132, the L-shaped legs 244 prevent axial displacement of the fluid connector 128 relative to the base 132, and the connector tabs 248 prevent rotation of the fluid connector 128 relative to the base 132.

Figure 14:
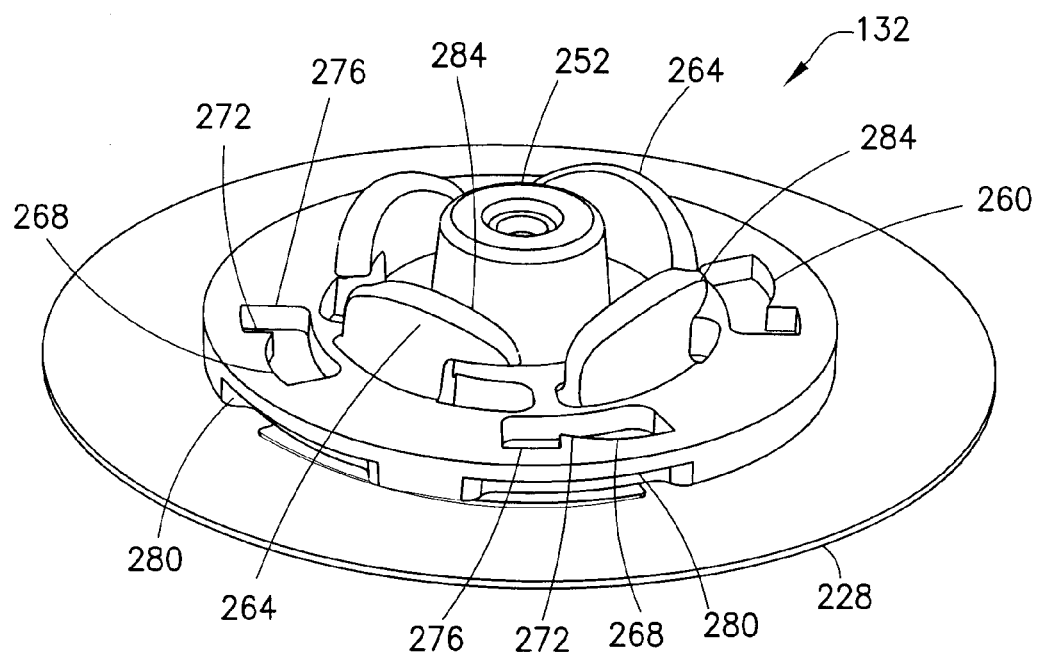
FIG. 14 is a perspective view of a base of the infusion set of FIG. 12.
Figure 15:
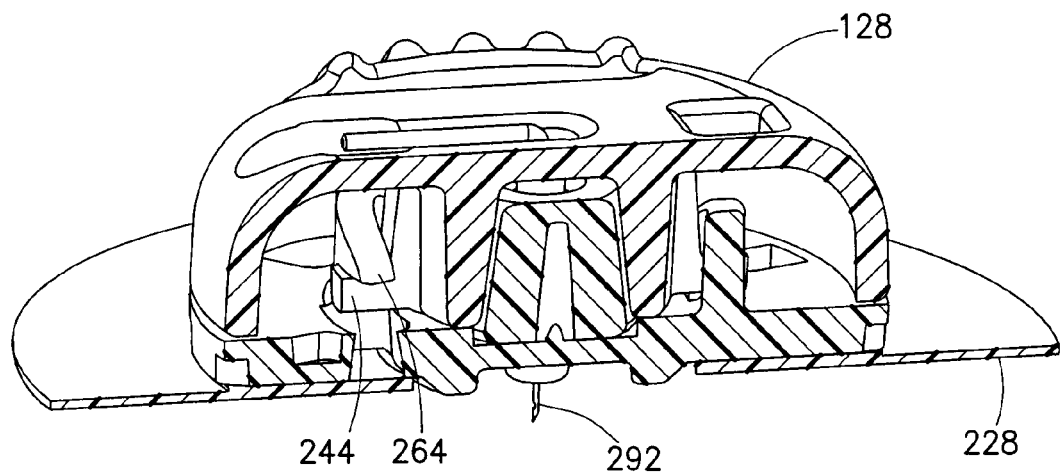
FIG. 15 is a cross-sectional view of the infusion set of FIG. 12 taken along the line 15-15 of FIG. 12.
Figure 16:
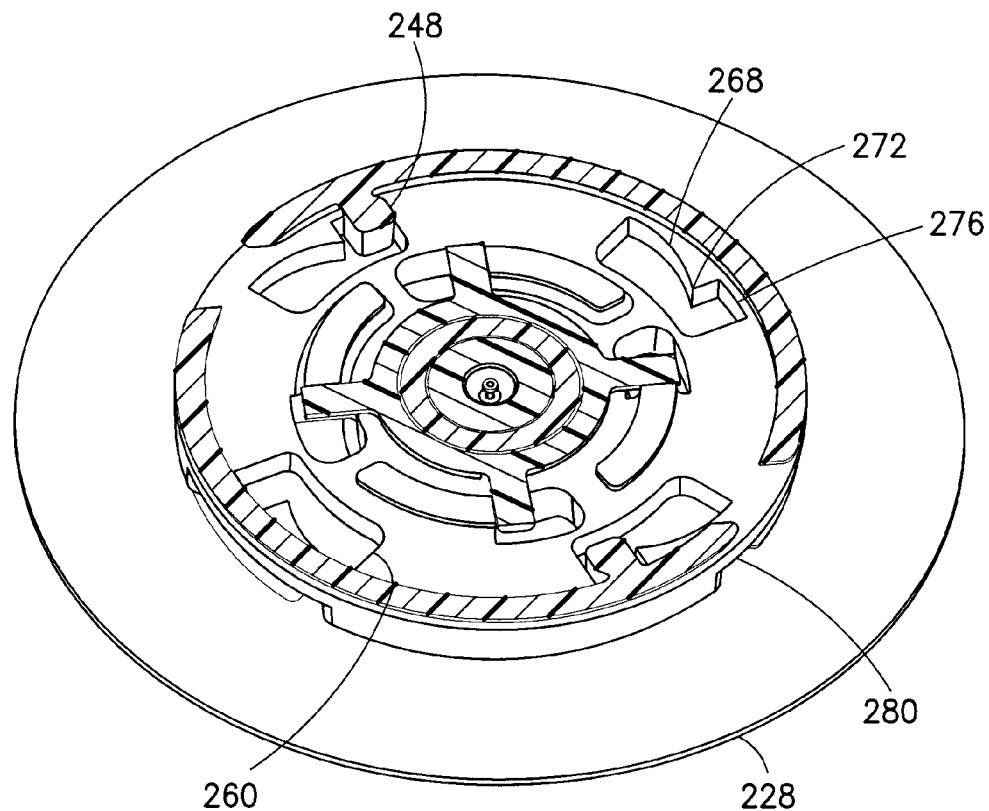
FIG. 16 is a cross-sectional view of the infusion set of FIG. 12 taken along the line 16-16 of FIG. 12.

As shown in FIGS. 14-16, the base 132 has a central conical guide 252 corresponding to the guide 236 of the fluid connector 128. According to one embodiment, the base guide 252 is a septum cap 252 that maintains the split septum 256 (shown, for example, in FIG. 17) within the base 132. Preferably, the septum 256 is made of a flexible material, such as isoprene. According to another embodiment, the guide 252 is integrally formed with the remainder of the base 132, and the top of the guide 252 is swaged over to maintain the septum 256 within the base.

Additionally, the base 132 has a plurality of horizontal locking structures 260 or locking channels 260 and a plurality of engaging protrusions or vertical locking members 264. The vertical locking members 264 are L-shaped and correspond to the L-shaped legs 244. The locking channels 260 are recessed from the top surface of the base 132 and correspond to the connector tabs 248. The respective correspondence of the locking channels 260 and the vertical locking members 264 with the connector tabs 248 and the L-shaped legs 244 provide multiple (four in this embodiment) different rotational orientations of the fluid connector 128 relative to the base 132. It will be understood by one skilled in the art that more or fewer orientations can be obtained by providing more or fewer connecting elements without departing from the scope of the present invention. Further, it will be understood by one skilled in the art, for example, that the fluid connector 128 can have fewer L-shaped legs 248 (for example, 1 or 2) and still provide multiple rotational orientations of the fluid connector 128 relative to the base 132.

The locking channels 260 have an insertion portion 268, a hook 272, and a locking portion 276. To connect the fluid connector 128 with the base 132, the patient inserts connector tabs 248 into the insertion portion 268 and subsequently rotates the fluid connector 128 relative to the base 132 until the connector tabs 248 pass the hooks 272 and snap into the locking portions 276. During this insertion, the bottom portions of the L-shaped legs 244 are inserted between the vertical locking members 264, and during the rotation, the bottom portions of the L-shaped legs 244 slide under the cantilevered arms 284 of the vertical locking members 264.

FIGS. 15 and 16 illustrate the respective interaction of the locking channels 260 and the vertical locking members 264 with the connector tabs 248 and the L-shaped legs 244 to lock the fluid connector 128 with the base 132. In addition to preventing axial removal of the fluid connector 128, as shown in FIG. 15, the vertical locking members 264 also prevent rotation of the fluid connector 128 in the clockwise rotational direction as viewed from the top. In addition, as shown in FIG. 16, once the connector tabs 248 are engaged with the locking portions 276, the locking portions 276 prevent rotation of the fluid connector in both the clockwise and counterclockwise rotational directions.

To remove the fluid connector 128 from the base 132, the user squeezes the wings in the fluid connector created by the cutouts 232. This action moves the connector tabs 248, which are disposed on the wings, radially inward, thereby disengaging the connector tabs 248 from the locking portions 276. Next the user rotates the fluid connector in the counterclockwise direction (i.e., opposite to the direction of the initial connection) and lifts the fluid connector 128 axially away from the base 132.

As shown, for example, in FIG. 14, the base 132 also includes a plurality of detents 280 recessed from the bottom side thereof for engaging the feet 192 of the cantilevered base arms 188 described previously.

Figure 17:
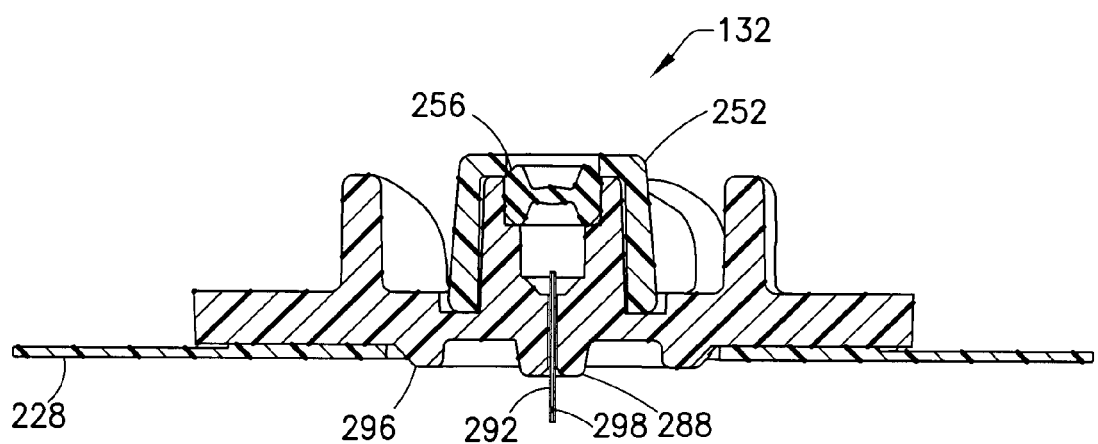
FIG. 17 is a cross-sectional view of the base of FIG. 14.
Figure 18:
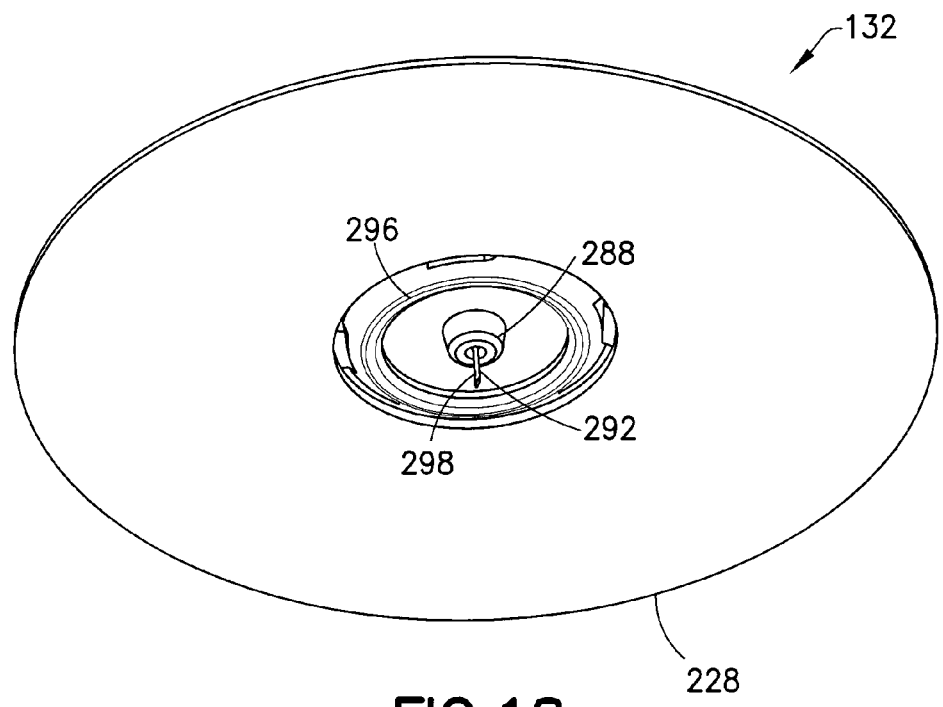
FIG. 18 is a perspective view of the bottom of the base of FIG. 14.

Because this is an intradermal device with the patient needle 292 penetrating the skin (for example, between 1-2 mm), it is important to accommodate bunching of the skin during injection. Turning to FIGS. 17 and 18, the bottom of the base 132 includes a central protrusion or cone 288 from which the patient needle 292 extends, and a conical outer ring 296 spaced from the central protrusion 288. This space between the outer ring 296 and the cone 288 (about 1-2 mm) provides for the deformation of the skin at the injection site and ensures proper seating and depth of the needle 292. The cone 288 also acts as a depth stop. According to one embodiment, the needle 292 is glued into the cone 288 from the proximal side (not the patient side) of the base 132 to ensure complete needle penetration into the patient. As shown in FIG. 17, both the cone 288 and the outer ring 296 extend beyond a central opening in the adhesive pad, with the cone 288 extending farther than the outer ring 296. Additionally, according to one embodiment, the needle 292 has a side port 298. The side port 298 can be in addition to or instead of an end port of the needle 292.

Figure 19:
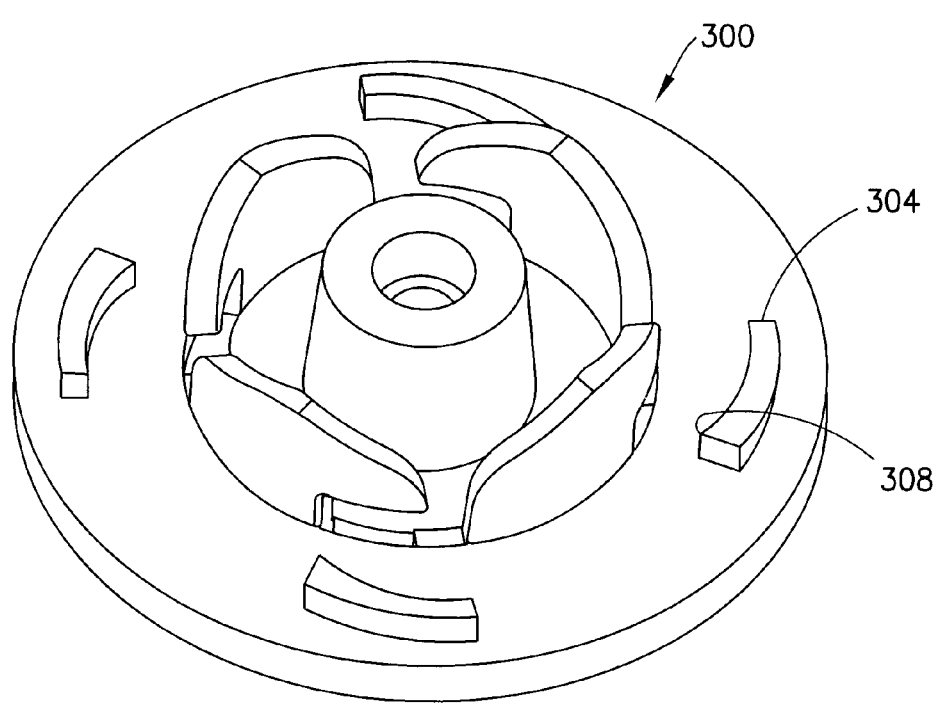
FIG. 19 is a perspective view of a base for an infusion set in accordance with another embodiment of the present invention.

FIG. 19 illustrates an alternative base with locking structures 304 that, in contrast to the previously-described recessed locking channels 260, protrude upward from the top surface of the base 300. In further contrast, rather than preventing rotation in both clockwise and counterclockwise directions, the locking structures 304 only prevent rotation in the counterclockwise direction when engaged with the connector tabs 248. Otherwise, the function and operation of the base 300 is substantially similar to the base 132.

Figure 20:
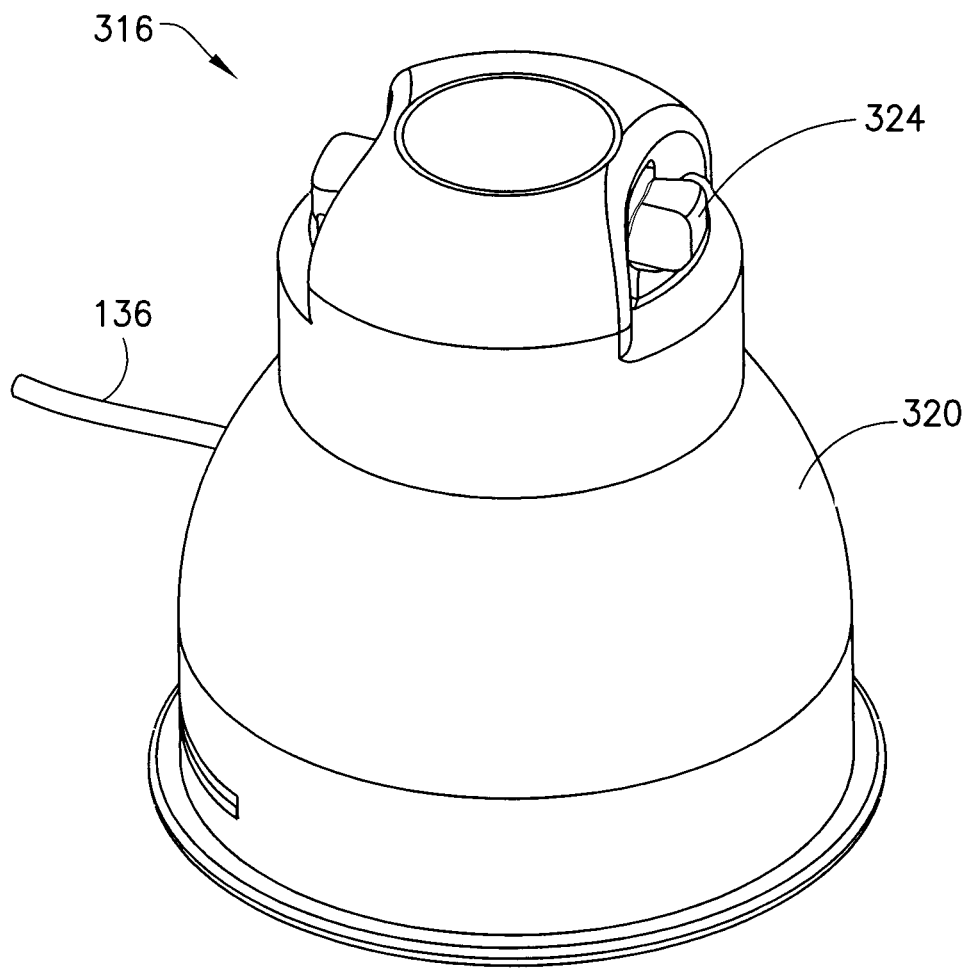
FIG. 20 is a perspective view of an insertion device assembly in accordance with another embodiment of the present invention.
Figure 21:
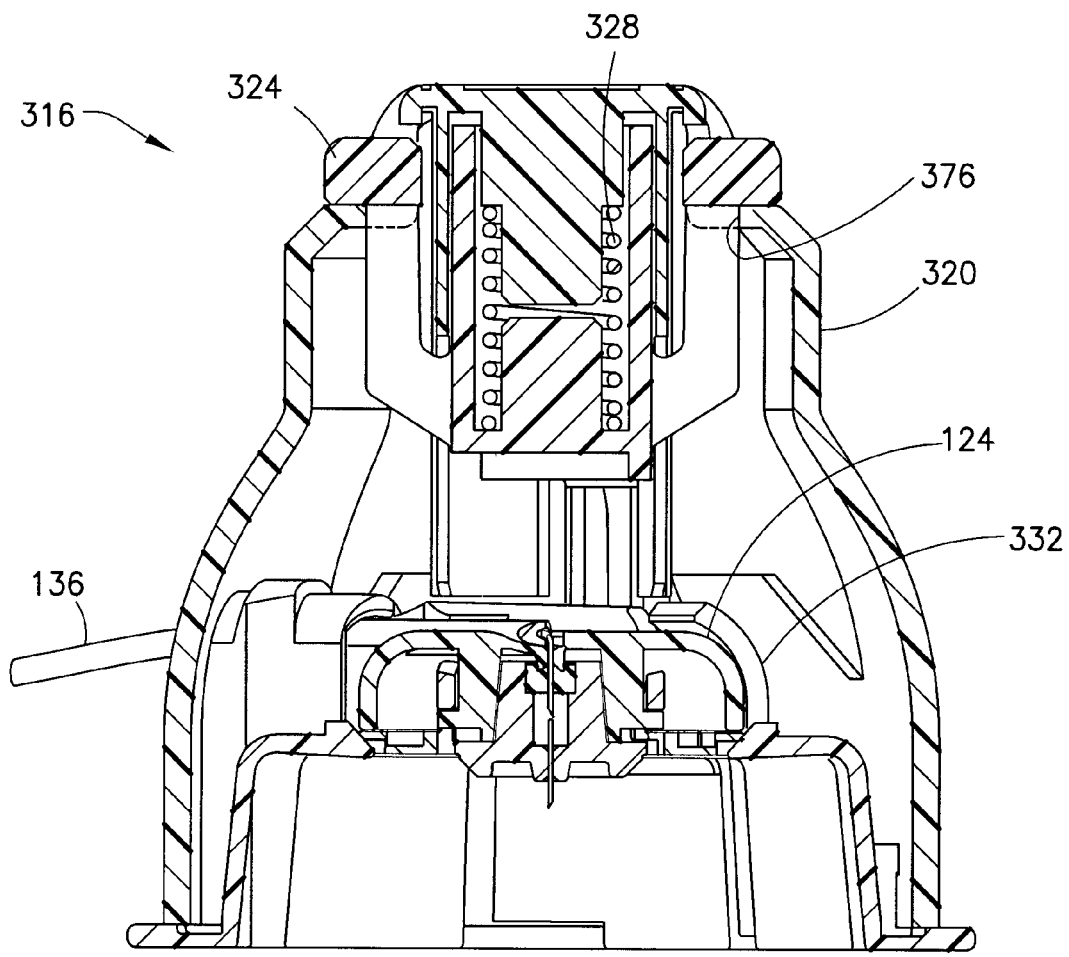
FIG. 21 is a cross-sectional view of the assembly of FIG. 20.

FIG. 20 is a perspective view of an insertion device assembly 316 in accordance with another embodiment of the present invention. As shown in FIGS. 20 and 21, the device 316 includes an inserter cap 320, a plunger 324, a biasing member or spring 328, an inserter base 332, and the infusion set 124 both actively and passively retained in the inserter base 332.

Figure 22:
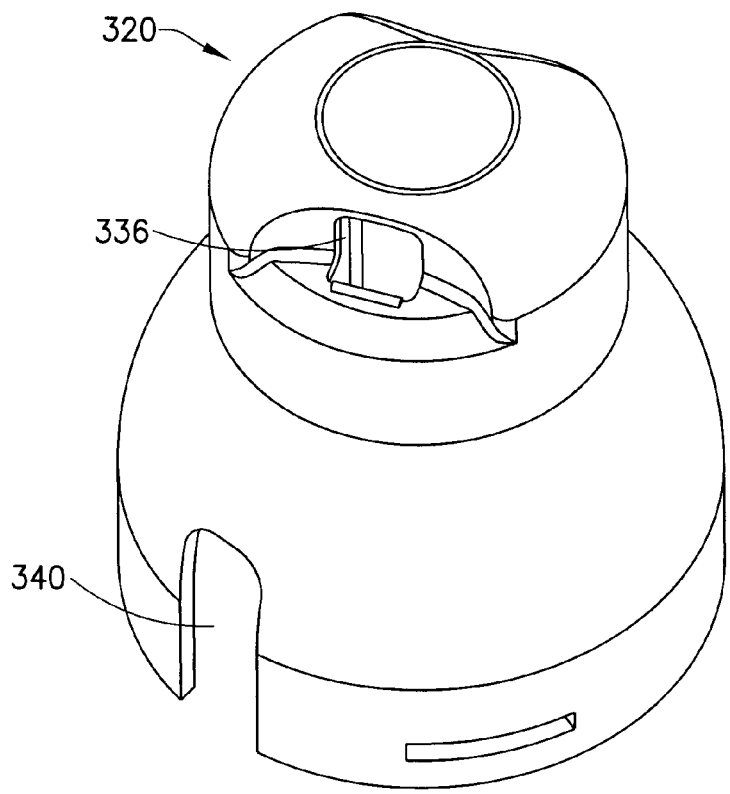
FIGS. 22 and 23 are, respectively, top and bottom perspective views of an inserter cap of the assembly of FIG. 20.
Figure 23:
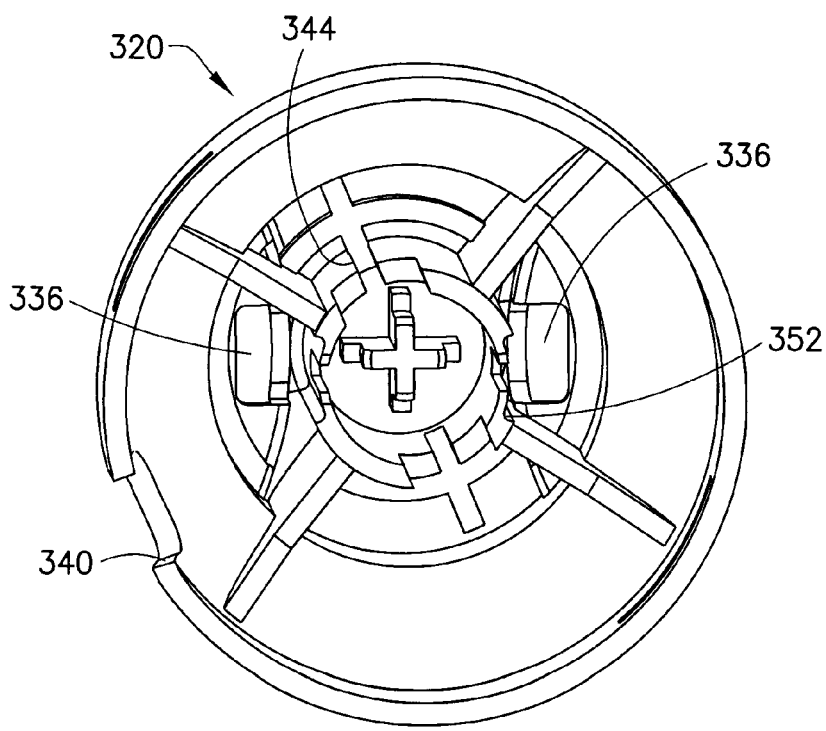
Figure 24:
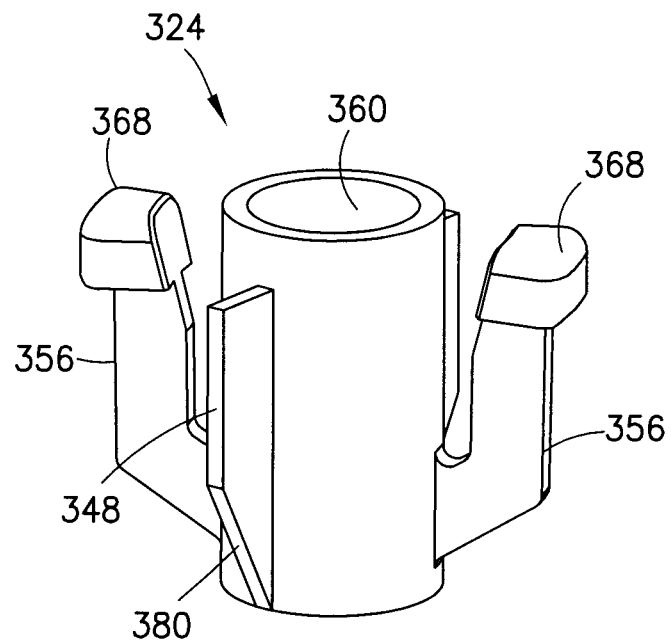
FIGS. 24-27 are perspective views of a plunger of the assembly of FIG. 20.
Figure 25:
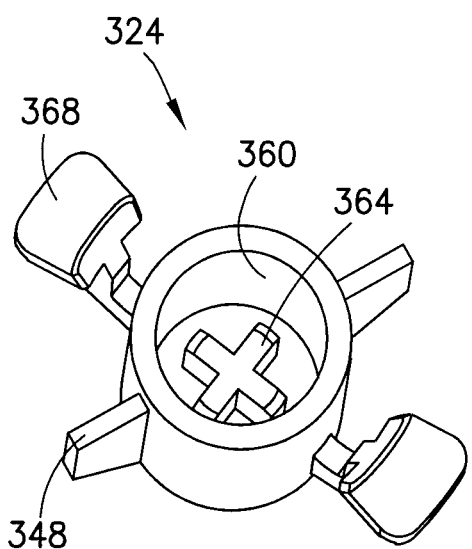

The inserter cap 320, the plunger 324, and the inserter base 332 can be manufactured using a two-piece molding process. As shown in FIGS. 22 and 23, the inserter cap 320 includes plunger openings 336 for portions of the plunger 324 to extend therethrough and a tubing opening 340 to provide free movement of the tubing 136. Inside of the inserter cap 320 there is a cruciform 340 for retaining an upper end of the spring 328, wing guide slots 344 for guiding wings 348 of the plunger 324, and arm guide slots 352 for guiding cantilevered arms 356 of the plunger 324. According to on embodiment, the inserter cap 320 snap-fits onto the inserter base 332.

Figure 26:
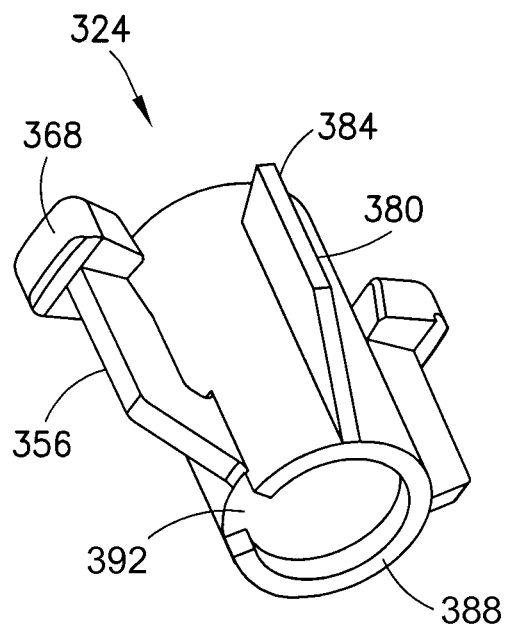
Figure 27:
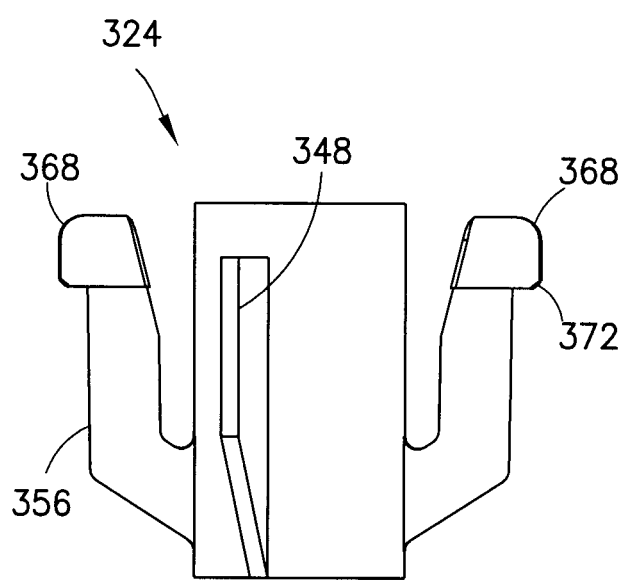

FIGS. 24-27 illustrate the plunger 324. The plunger 324 includes an internal cavity 360 with a cruciform 364 disposed in the bottom thereof for retaining the bottom of the spring 328. Pushbuttons 368 disposed at the free ends of the cantilevered arms 356 provide a patient interface for activating the inserter. As best shown in FIG. 27, each of the pushbuttons 368 includes a chamfer 372 at an external bottom portion thereof to ease movement of the pushbuttons 368 past a lip 376 (see FIG. 21) of the inserter cap 320. The wings 348 have a ramp surface 380 and a guiding surface 384. As shown in FIG. 26, the bottom of the plunger 324 includes a hammer portion or striking surface 388 for impacting or striking the infusion set 124. The hammer portion 388 has a cutout 392 to accommodate the tubing 136.

Figure 28:
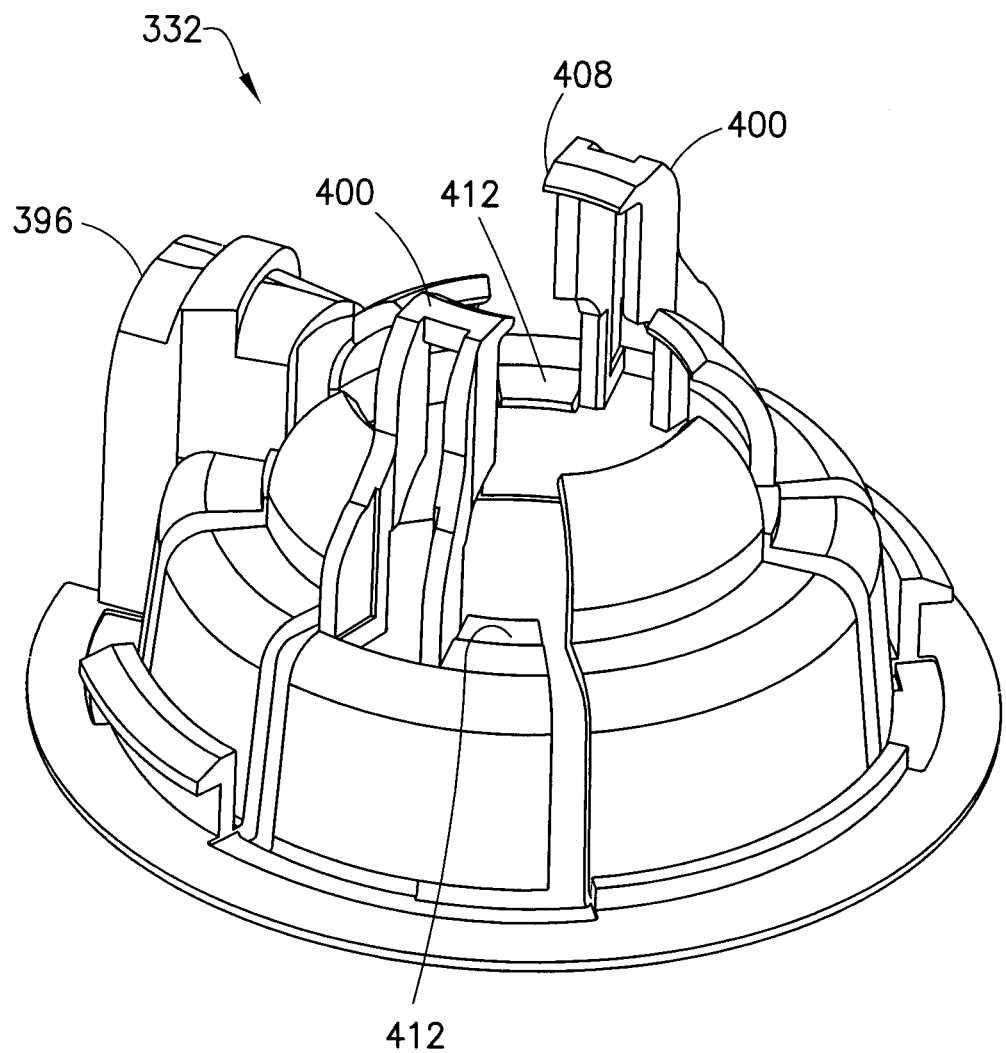
FIGS. 28-31 are perspective views of an inserter base of the assembly of FIG. 20.
Figure 29:
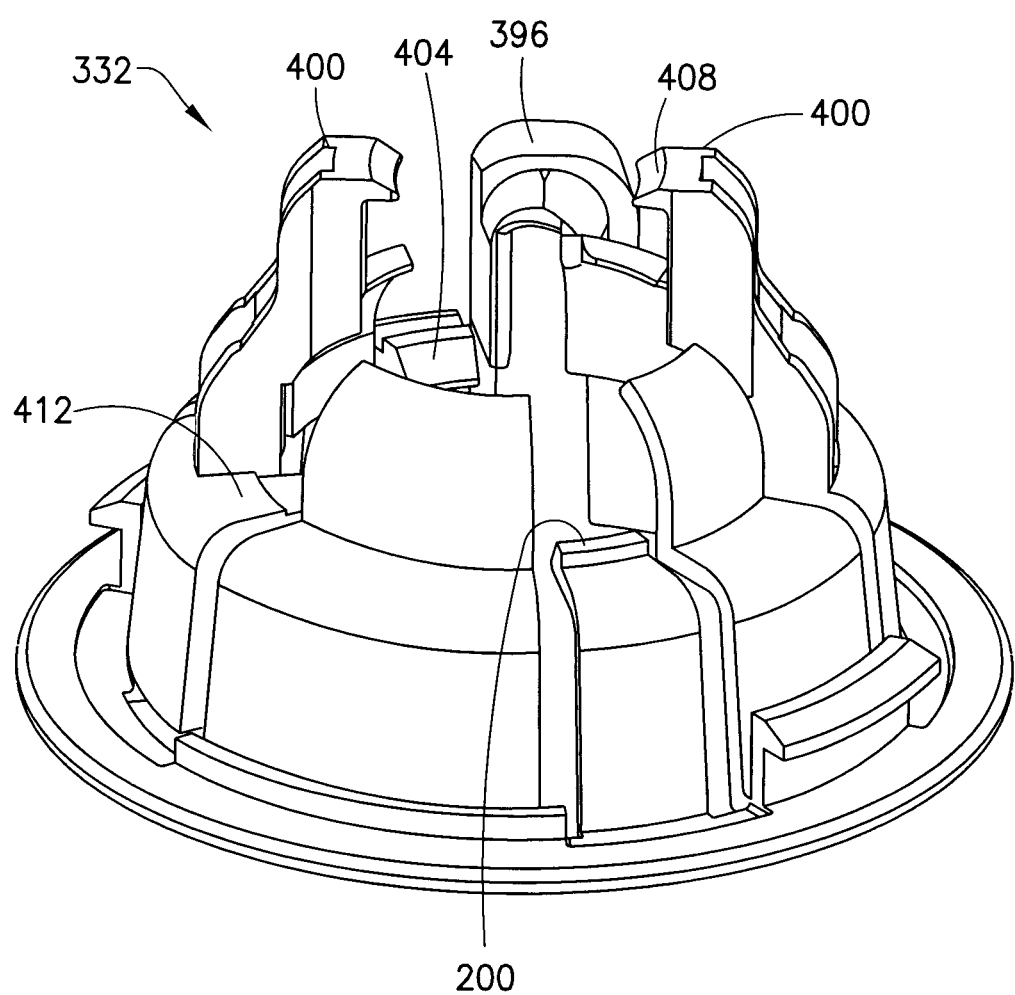
Figure 30:
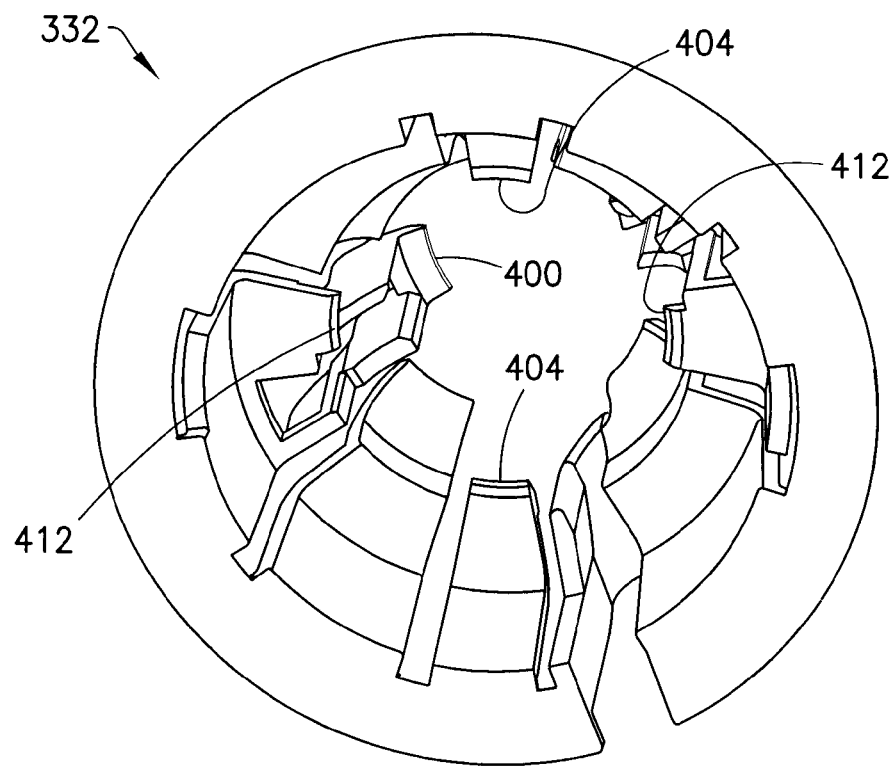
Figure 31:
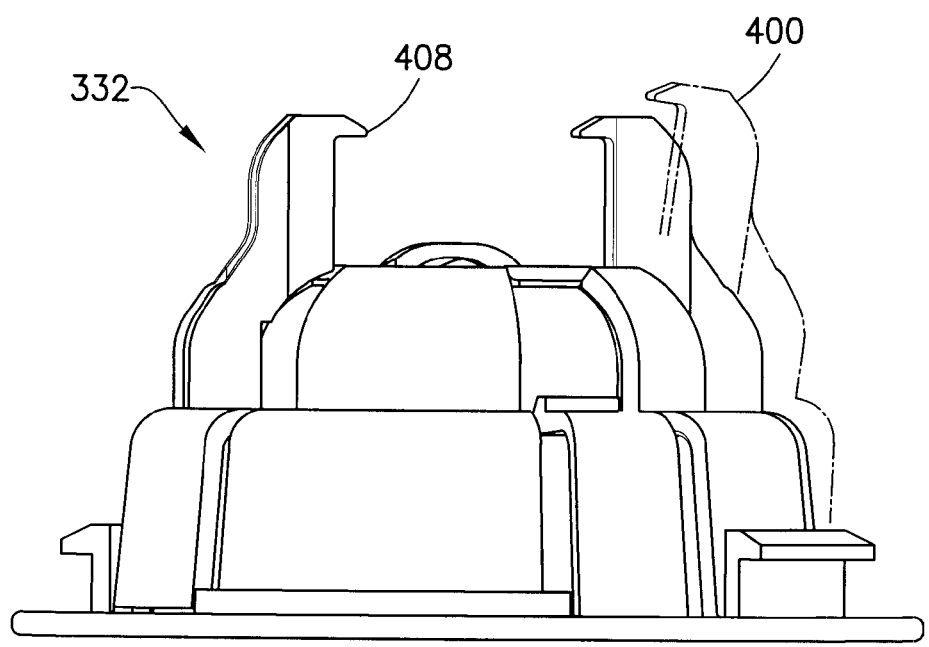

FIGS. 28-31 illustrate the inserter base 332. The inserter base 332 includes a tubing opening 396 corresponding to the tubing opening 340 of the inserter cap 320, to accommodate the tubing 136. The inserter base 332 also includes active and passive infusion set retainers. Flexible, cantilevered retainer arms 400 are the active retainers and flexible, cantilevered arms or tabs 404 are the passive retainers. The cantilevered retainer arms 400 have hook ends 408 disposed at the top-most unsupported end thereof, and, as shown in FIGS. 28-30, the retainer arms 400 also have feet 412 for engaging the infusion set 124. According to one embodiment, the arms 400 and the tabs 404 hold the infusion set 124 spaced apart from the patient's skin. According to another embodiment, the cannula 292 can contact the patient's skin.

Figure 32:
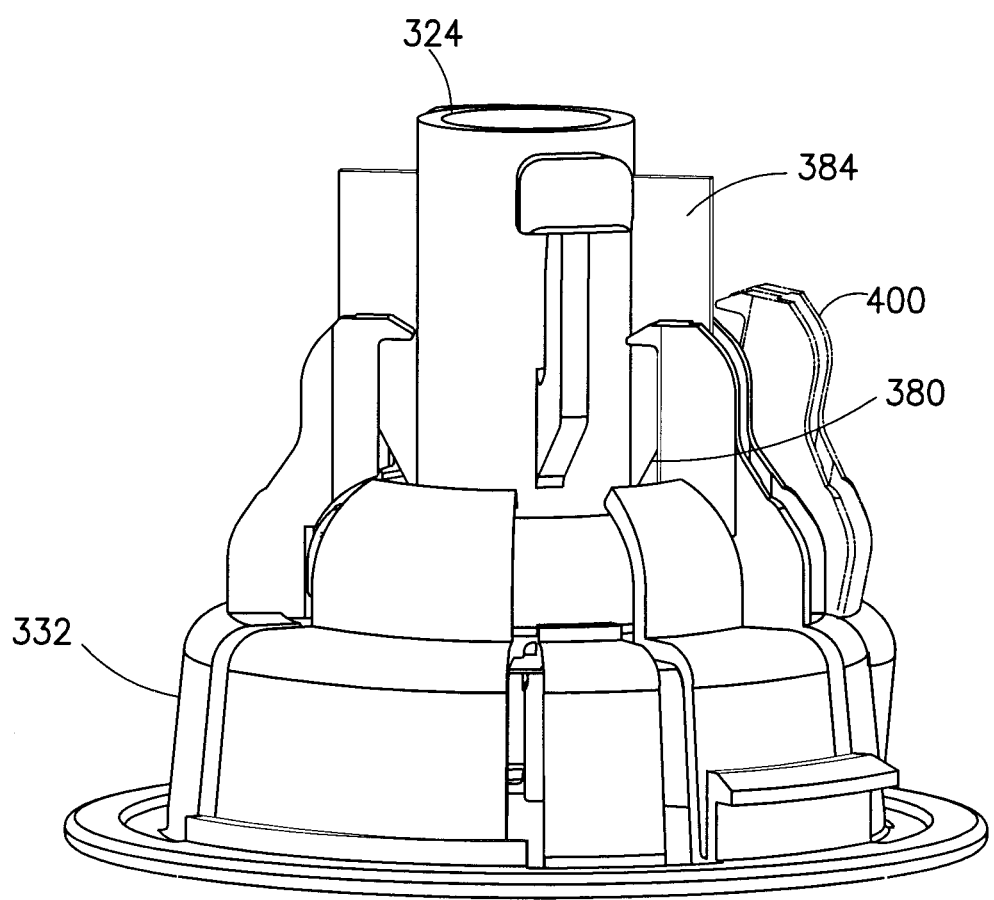
FIGS. 32 and 33 are perspective views of the plunger and inserter base of the assembly of FIG. 20 illustrating their operation.
Figure 33:
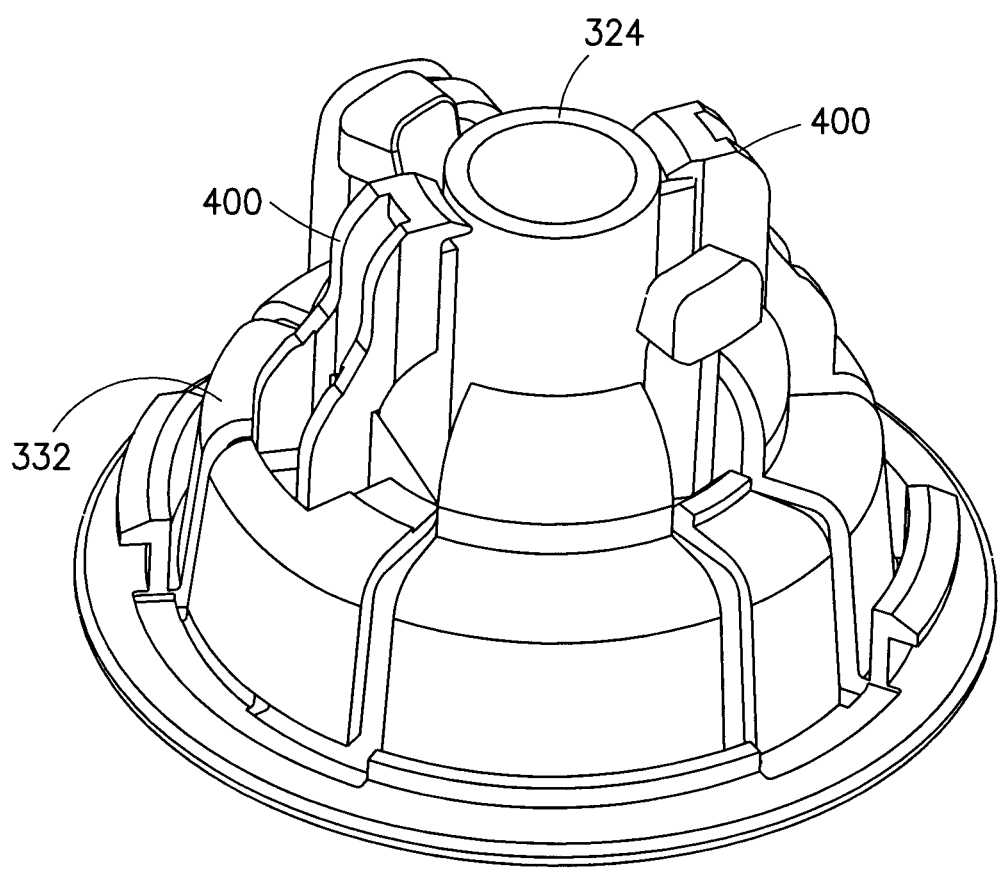

When the user inwardly presses the pushbuttons 368 of the plunger 324 to clear the lip 376, the spring 328 forces the plunger 324 downward. During this downward movement, the ramp surfaces 380 and the guiding surfaces 384 of the wings 348 outwardly displace the retainer arms 400 of the inserter base 332, as shown on the right-hand side of FIGS. 31 and 32. This action also disengages the feet 412 from the detents 280 in the infusion set 124. Subsequently, but prior to the plunger 324 striking the infusion set 124, the guiding surfaces 384 pass the hook ends 198 of the retaining arms 400 and the retaining arms 400 return to their initial position, as shown in FIG. 33.

Thus, in the last portion of the stroke of the plunger 324, the entire force on the plunger 324 is from the spring 328. In other words, there is no frictional resistance on the plunger 324 after the retaining arms 400 move to their initial positions, until the striking surface 388 of the plunger 324 strikes the infusion set 124. The action of the plunger 324 striking the infusion set 124 releases the infusion set 124 from the passive cantilevered tabs 404 and provides the infusion set 124 with sufficient energy to drive the metal intradermal hub needle 292 into the patient's skin. According to one embodiment, after release from the inserter base 332, the infusion set 124 travels free from the inserter base 332 and the plunger 324. Additionally, although the insertion device assembly 316 is depicted with the infusion set 124, it will be understood by one skilled in the art that other infusion sets can be used without departing from the scope of the present invention.

According to one embodiment, the insertion device assembly 316 is a single-use device. According to an alternative embodiment, the inserter portion of the insertion device assembly 316 is reusable.

Figure 34:
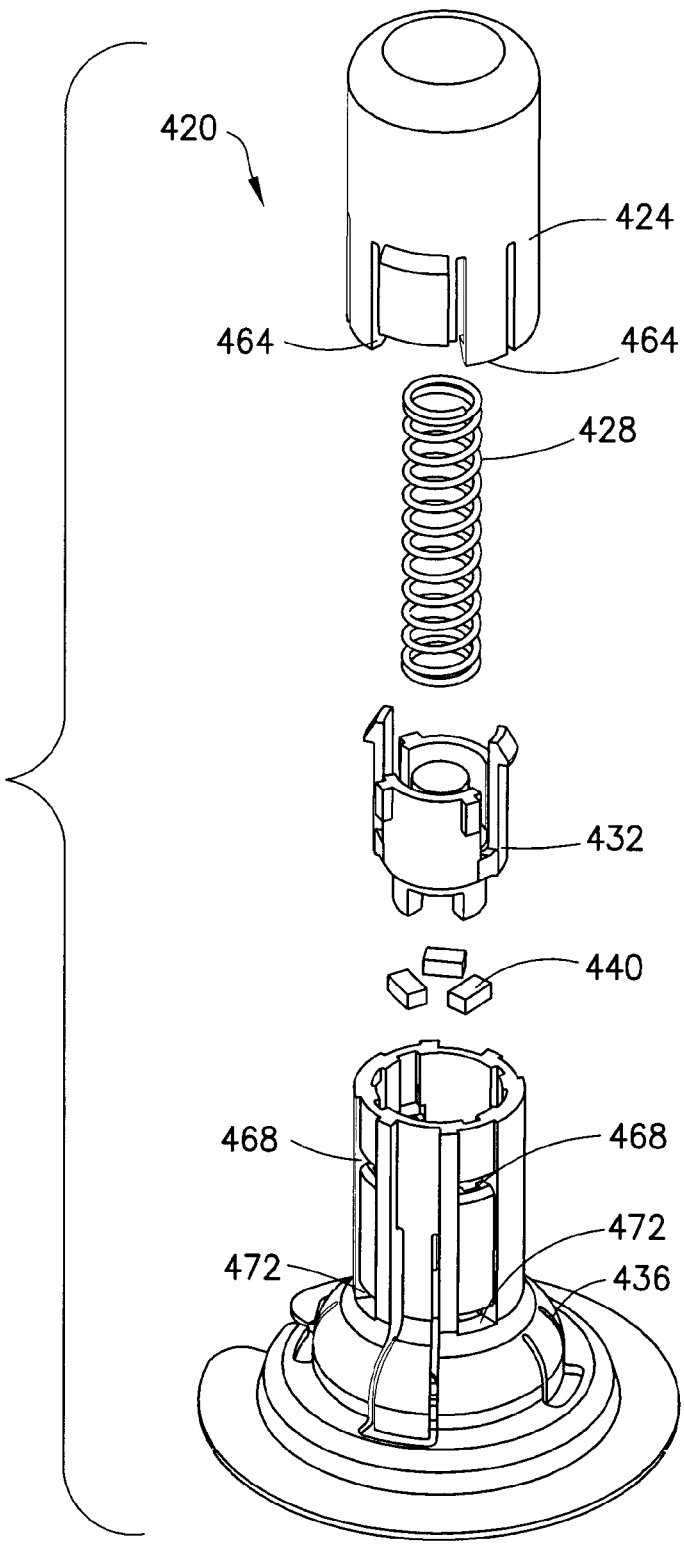
FIG. 34 is an exploded view of an insertion device assembly in accordance with another embodiment of the present invention.
Figure 35:
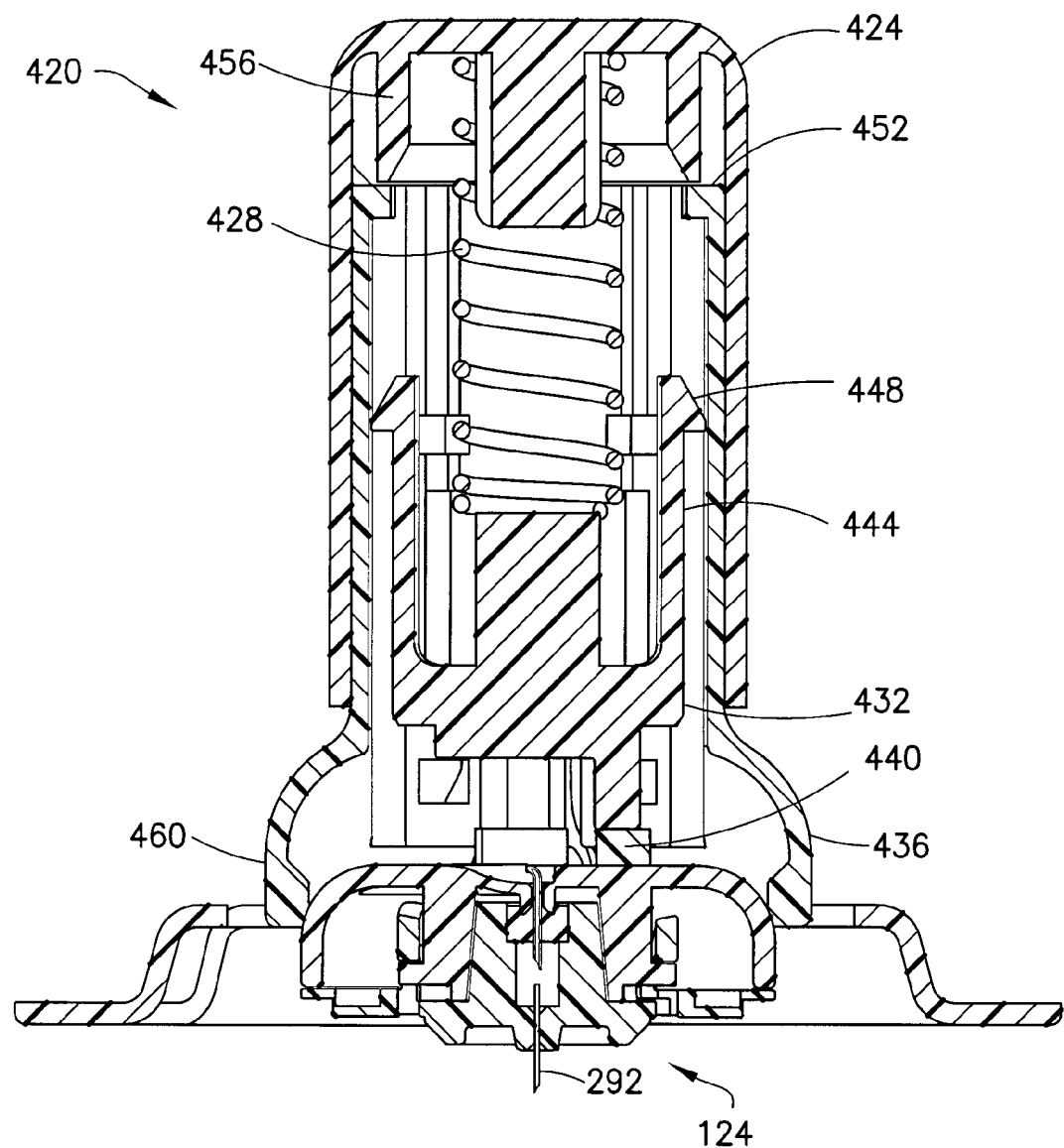
FIG. 35 is a cross-sectional view of the assembly of FIG. 34 subsequent to activation.

FIG. 34 is an exploded view of an insertion device assembly 420 in accordance with another embodiment of the present invention and FIG. 35 is a cross-sectional view of the assembly 420 subsequent to activation. The assembly includes an inserter cap or button 424, a biasing member or spring 428, a plunger 432, an inserter base 436, and the infusion set 124. According to one embodiment, the assembly 420 also includes resilient pads 440 to reduce the shock of the impact of the plunger 432 on the infusion set 124.

As shown in FIG. 35, both the button 424 and the plunger 432 have central protrusions for mounting the spring 428. Additionally, the plunger 432 has a pair of cantilevered arms 444 with hooks 448 disposed at the unsupported ends thereof. The inserter base 436 includes retaining structures 452 at the top thereof for retaining the hooks 448 when the plunger 432 is in the pre-activated position. Further, the button 424 includes an internal activating structure 456. According to one embodiment, the activating structure is a pair of cantilevered arms 456 with tapered ends. According to another embodiment, the activating structure 456 is a hollow cylinder 456 with a tapered distal rim.

According to one embodiment, retaining arms 460 hold the infusion set 124 in a single axial position relative to the base 436 that is spaced apart from the patient's skin. According to another embodiment, the cannula 292 can contact the patent's skin.

In use, the patient first removes the backing from the adhesive pad 228, primes the infusion set, and then places the assembly 420 over the desired infusion site. When the user depresses the button 424, the tapered end of the activating structure 456 dislodges the hooks 448 from the retaining structures 452, and the plunger travels distally under the force of the spring 428. Upon impacting the infusion device 124, the plunger 432 imparts momentum to the infusion set 124 and releases the infusion set 124 from the retaining arms 460 of the inserter base 436 that retain the infusion set prior to the impact of the plunger 432. In other words, as in the other described inserters, the impact of the plunger 432 releases the infusion set 124 from the inserter. Thus, as in previously-described inserters, after activation, the infusion set 124 is completely free of the inserter. The imparted momentum drives the needle 292 into the patient's skin.

According to one embodiment, the button 424 includes hooks 464 that latch into openings 468 in the inserter base 436 to prevent the spring 428 from dislodging the button 424 from the assembly 420. Additionally, once the button 424 is depressed to activate the assembly 420, the hooks 464 latch into openings 472. This latching with openings 472 secures the button 424 to the inserter base 436 to prevent re-use of the inserter. According to another embodiment, the inserter is re-usable. Further, although the insertion device assembly 420 is depicted with the infusion set 124, it will be understood by one skilled in the art that other infusion sets can be used without departing from the scope of the present invention.

Figure 36:
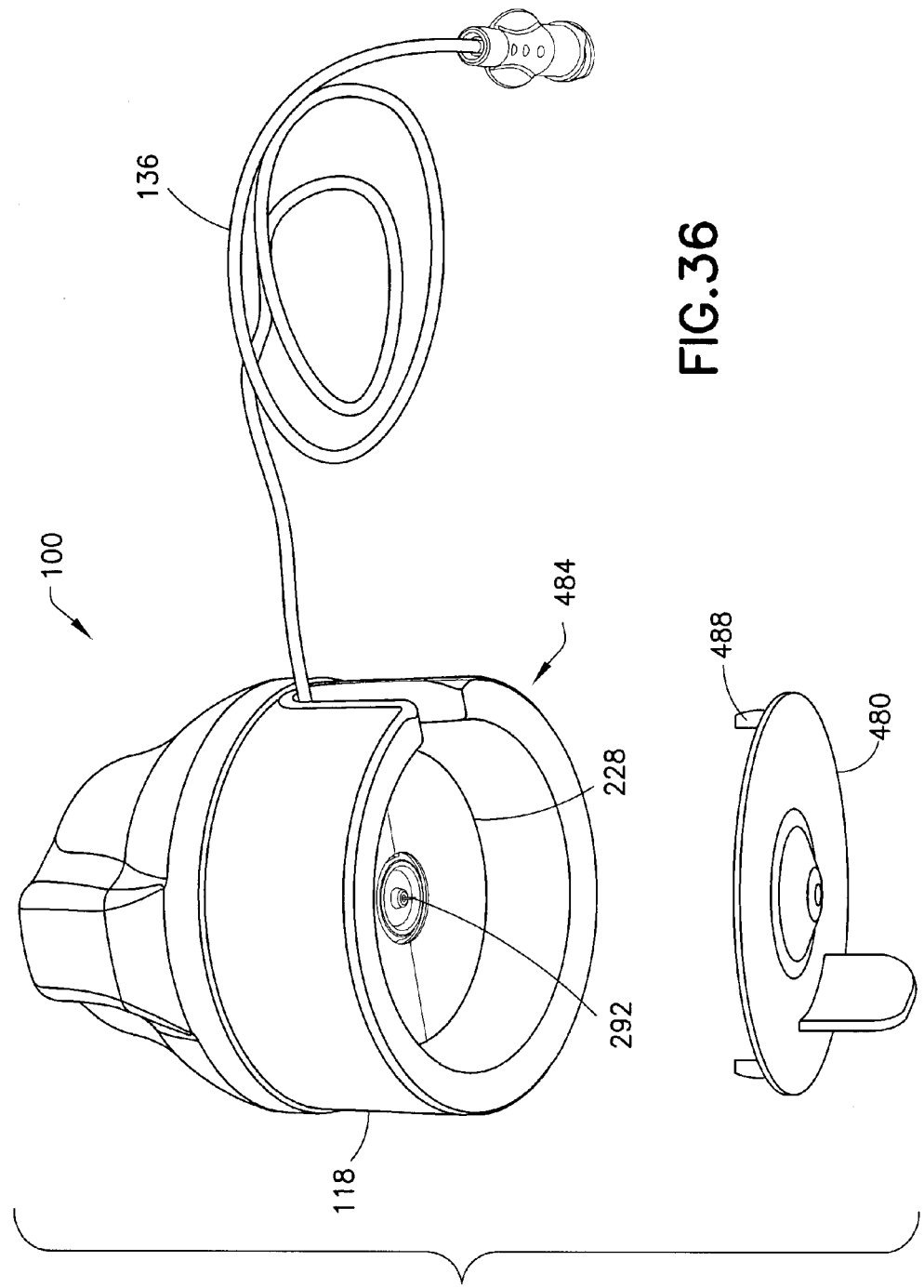
FIG. 36 is a perspective view of the assembly of FIG. 1 with a cannula guard tray in accordance with an embodiment of the present invention.

In addition to the previously-described embodiments, other features can be employed with the inventive insertion device assemblies. For example, FIG. 36 illustrates the insertion assembly 100 of FIG. 1 with the membrane 208 already removed. In the state depicted in FIG. 36, a majority of the tubing 136 and a cannula guard tray 480 have also been removed from a cavity 484 in the inserter housing 118. Prior to its removal from the cavity 484, the tray 480 protects the cannula 292 and separates the tubing 136 from the infusion set 124. In the embodiment shown, in FIG. 36, the adhesive pad 228 does not have an adhesive backing, and thus, in addition to protecting the cannula 292, the tray 480 protects the adhesive pad 228 by preventing contact with the tubing 136. A feature, such as standoffs 488 space the tray 480 from the adhesive pad 228. According to another embodiment, the feature preventing contact between the adhesive pad 228 and the tray 480 can be on the inserter housing 118. According to yet another embodiment, the tray 480 is connected with an adhesive backing, and by removing the tray 480, the user also removes the adhesive backing from the adhesive pad 228.

Although the previously-described embodiments relate to intradermal infusion sets, the principles of the present invention are also applicable to other types of infusion sets, for example, subcutaneous infusion sets in which the patient cannula consists of a soft plastic catheter that is inserted with the aid of a rigid metal introducer needle.

Although only a few embodiments of the present invention have been shown and described, the present invention is not limited to the described embodiments. Instead, it will be appreciated by those skilled in the art that changes may be made to these embodiments without departing from the principles and spirit of the invention, the scope of which is defined by the appended claims and their equivalents.

What is claimed is:

1. An infusion set inserter, comprising:
   an inserter housing comprising at least one flexible arm for holding an infusion set in a single axial position prior to insertion of at least a portion of a cannula of the infusion set, the inserter housing having a surface for contacting the patient's skin, and the infusion set having a body with an upper surface;
   a movable plunger disposed within the inserter housing for releasing the infusion set from the inserter housing, directly striking the upper surface of the infusion set, and imparting momentum to the infusion set to insert the cannula into the patient's skin; and
   a biasing element biasing the plunger toward the activated position;
   wherein:
   the plunger is movable between a pre-activated position and an activated position;
   the plunger is spaced apart from the infusion set in the pre-activated position; and
   the plunger comprises at least one cantilevered arm adapted to engage the inserter housing to maintain the plunger in the pre-activated position and to engage the inserter housing to retain the plunger within the inserter housing in the activated position.

2. The inserter according to claim 1, wherein the inserter housing includes a housing tubing opening to accommodate tubing of the infusion set prior to and subsequent to activation of the inserter.

3. The inserter according to claim 2, wherein the plunger includes a plunger tubing opening to accommodate the infusion set tubing.

4. The inserter according to claim 1, wherein the flexible arm holds the infusion set spaced apart from a patient's skin prior to insertion.

5. The inserter according to claim 1, wherein the cannula extends from a bottom surface of the infusion set, and the at least one flexible arm holds at least the bottom surface of the infusion set spaced apart from a patient's skin prior to insertion.

6. An infusion set inserter, comprising:
   an inserter housing comprising at least one flexible arm for holding an infusion set in a single axial position prior to insertion of at least a portion of a cannula of the infusion set, the inserter housing having a surface for contacting the patient's skin;
   a movable plunger disposed within the inserter housing for releasing the infusion set from the inserter housing, impacting the infusion set, and imparting momentum to the infusion set to insert the cannula into the patient's skin; and
   a biasing element biasing the plunger toward the activated position;
   wherein the plunger selectively moves between a pre-activated position and an activated position;
   wherein the at least one flexible arm comprises a plurality of cantilevered, flexible arms; and
   wherein upon movement of the plunger from the pre-activated position to the activated position at least one of the cantilevered arms is displaced away from the infusion set prior to the impact of the plunger on the infusion set.

7. The inserter according to claim 6, wherein in the pre-activated position, the plunger biases the cantilevered arms toward the infusion set, and movement of the plunger from the pre-activated position to the activated position releases the at least one cantilevered arm to displace away from the infusion set prior to the impact of the plunger on the infusion set.

8. The inserter according to claim 6, wherein the cantilevered arms are biased toward the infusion set and movement of the plunger from the pre-activated position to the activated position displaces the at least one cantilevered arm away from the infusion set prior to the impact of the plunger on the infusion set.

9. The inserter according to claim 6, wherein prior to displacement, the cantilevered arms engage a bottom surface of the infusion set with a hook disposed at a distal end of the cantilevered arm.

10. The inserter according to claim 6, wherein during movement of the plunger from the pre-activated position to the activated position, the cantilevered arms maintain engagement with the infusion set prior to the impact of the plunger on the infusion set.

11. The inserter according to claim 10, wherein the cantilevered arms engage a bottom surface of the infusion set with a hook disposed at a distal ends of the flexible arm.

12. The inserter according to claim 10, wherein at least one of the cantilevered arms is biased toward the infusion set.

13. An infusion set inserter, comprising:
an inserter housing comprising at least one flexible arm for holding an infusion set in a single axial position prior to insertion of at least a portion of a cannula of the infusion set, the inserter housing having a surface for contacting the patient's skin;
a movable plunger disposed within the inserter housing for releasing the infusion set from the inserter housing, impacting the infusion set, and imparting momentum to the infusion set to insert the cannula into the patient's skin; and
a biasing element biasing the plunger toward the activated position;
wherein the plunger selectively moves between a pre-activated position, in which the plunger prevents the at least one flexible arm from moving away from the infusion set, and an activated position, in which the plunger does not prevent the at least one flexible arm from moving away from the infusion set.

14. The inserter according to claim 1, wherein the inserter is reusable.

15. The inserter according to claim 1,
wherein the inserter housing comprises:
an inserter base including the surface for contacting the patient's skin; and
an inserter cap secured to the inserter base and having a plunger-retaining structure for retaining the plunger in the pre-activated position prior to activation.

16. The inserter according to claim 15, wherein the inserter base, the inserter cap, and the plunger are two-piece moldable.

17. The inserter according to claim 1,
wherein the inserter housing comprises a user-activatable releasing structure to selectively release the plunger from engagement with the inserter housing to move from the pre-activated position to the activated position.

18. The inserter according to claim 17, wherein the user-activatable releasing structure comprises the at least one cantilevered arm.

19. The inserter according to claim 18, further comprising a removable safety cover that prevents movement of the cantilevered arm.

20. The inserter according to claim 17, wherein the inserter housing comprises:
an inserter base including the surface for contacting the patient's skin; and
an inserter cap slidably disposed on the inserter base;
wherein the user-activatable releasing structure comprises one of an arm or a cylinder internally depending distally from a proximal end of the inserter cap that releases the plunger from engagement with the inserter base upon distal movement of the inserter cap.

21. The inserter according to claim 1,
wherein inserter housing includes a plunger-retaining structure to engage the plunger and retain the plunger within the inserter housing in the activated position.

22. An infusion set inserter, comprising:
an inserter housing comprising at least one flexible arm for holding an infusion set in a single axial position prior to insertion of at least a portion of a cannula of the infusion set, the inserter housing having a surface for contacting the patient's skin;
a movable plunger disposed within the inserter housing for releasing the infusion set from the inserter housing, impacting the infusion set, and imparting momentum to the infusion set to insert the cannula into the patient's skin; and
a biasing element biasing the plunger toward the activated position;
wherein the plunger selectively moves between a pre-activated position and an activated position;
wherein the plunger comprises at least one cantilevered arm for engaging the inserter housing in both the pre-activated position and the activated position; and
wherein the plunger further comprises a ring structure for biasing at least one of the flexible arms toward the infusion set in the pre-activated position and releasing the at least one of the flexible arms prior to the impact of the plunger on the infusion set.

23. An infusion set inserter, comprising:
an inserter housing comprising at least one flexible arm for holding an infusion set in a single axial position prior to insertion of at least a portion of a cannula of the infusion set, the inserter housing having a surface for contacting the patient's skin;
a movable plunger disposed within the inserter housing for releasing the infusion set from the inserter housing, impacting the infusion set, and imparting momentum to the infusion set to insert the cannula into the patient's skin; and
a biasing element biasing the plunger toward the activated position;
wherein the plunger selectively moves between a pre-activated position and an activated position;
wherein the plunger comprises at least one cantilevered arm for engaging the inserter housing in both the pre-activated position and the activated position; and
wherein the plunger further comprises a ring structure for preventing the at least one flexible arm from moving away from the infusion set in the pre-activated position and permitting the at least one flexible arm to move away from the infusion set prior to the impact of the plunger on the infusion set.

24. An infusion set inserter, comprising:
an inserter housing for holding an infusion set prior to insertion of at least a portion of a cannula of the infusion set, the inserter housing having a surface for contacting the patient's skin, and the infusion set having a body with an upper surface;

a movable plunger movable between a pre-activated position and an activated position, the plunger being disposed within the inserter housing for releasing the infusion set from the inserter housing, directly striking the upper surface of the infusion set, and imparting momentum to the infusion set to insert the cannula into the patient's skin, the plunger comprising a cantilevered arm with a hook disposed at the free end thereof for contacting the inserter housing to selectively retain the plunger in the pre-activated position prior to activation and to engage the inserter housing to retain the plunger within the inserter housing in the activated position; and a biasing element biasing the plunger toward the activated position;

wherein the plunger is spaced apart from the infusion set in the pre-activated position.

* * * * *